United States Patent [19]

Abrams et al.

[11] Patent Number: 6,004,905

[45] Date of Patent: Dec. 21, 1999

[54] HYPERABAS: BIOLOGICALLY ACTIVE ABSCISIC ACID ANALOGS WITH UNSATURATED CARBON SUBSTITUENTS AT THE 8'-METHYL OR 9'-METHYL CARBON ATOMS

[75] Inventors: Suzanne R. Abrams; John J. Balsevich; Adrian J. Cutler, all of Saskatoon; Bo Lei, North York; Patricia A. Rose, Saskatoon, all of Canada

[73] Assignee: National Research Council of Canada, Ottawa, Canada

[21] Appl. No.: 09/091,502

[22] PCT Filed: Dec. 20, 1996

[86] PCT No.: PCT/CA96/00854

§ 371 Date: Sep. 22, 1998

§ 102(e) Date: Sep. 22, 1998

[87] PCT Pub. No.: WO97/23441

PCT Pub. Date: Jul. 3, 1997

[51] Int. Cl.$^6$ .......................... A01N 35/02; A01N 35/06; C07C 49/21; C07C 47/42
[52] U.S. Cl. .......................... 504/348; 504/193; 568/343; 568/378; 568/447; 562/508; 560/126
[58] Field of Search .................................... 568/447, 378, 568/446, 823, 343, 347, 356; 562/507, 508; 560/126, 128; 504/348, 193, 201, 207, 288, 291, 320, 325; 435/422, 420

[56] References Cited

U.S. PATENT DOCUMENTS 4,209,530  6/1980  Visscher .................................... 424/317
5,201,931  4/1993  Abrams et al. .......................... 504/291
5,518,995  5/1996  Abrams et al. .......................... 504/348

*Primary Examiner*—Shailendra Kumar
*Assistant Examiner*—Sreeni Padmanabhan
*Attorney, Agent, or Firm*—J. Wayne Anderson

[57] ABSTRACT

The invention disclosed relates to a new class of abscisic acid (ABA) analogs of formula I

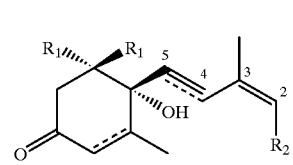

wherein one of $R_1$ is alkenyl, alkynyl, aryl, cycloalkenyl, other farther substituted carbon chain including deuterium containing residues, and carbon containing substituents with heteroatoms and halogens and the other is methyl, and wherein the five member carbon side chain includes a methyl group at C3, with C5 attached to the ring as shown, including a trans double bond at the C4–C5 position, or a triple bond at this position, and either a cis or a trans double bond at the C2–C3 position, and $R_2$ is $CH_2OH$, CHO, COOH, COO alkyl, or derivatives thereof, and wherein the cyclohexanone ring double bond may also be reduced and to a novel process for synthesizing such ABA analogs.

23 Claims, 20 Drawing Sheets

HYPERABAS: BIOLOGICALLY ACTIVE ABSCISIC ACID ANALOGS WITH UNSATURATED CARBON SUBSTITUENTS AT THE 8'-METHYL OR 9'-METHYL CARBON ATOMS

This is the U.S. National Stage Application of PCT/CA96/00854 filed Dec. 20, 1996.

BACKGROUND OF THE INVENTION

This invention relates to a new class of abscisic acid (ABA) analogs which have been altered at the 8'-or 9'-carbon atom, and to a novel process for synthesizing such ABA analogs.

1. Background

Abscisic acid is a plant hormone that regulates diverse aspects of plant growth including development and germination of seeds, transpiration, and responses to stress.

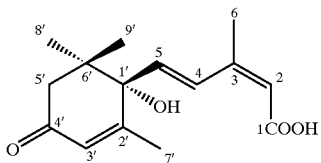

abscisic acid, (+)-ABA (with numbering system for carbon atoms and conformation representation)

The hormone itself has found limited use as an externally applied plant growth regulator because of uptake and stability problems and because of cost.

Moreover, examination of the mechanisms of ABA action, identification of receptor proteins, and cellular localization of the hormone have been restricted by rapid turnover of the hormone in plants. Similarly, agricultural uses of applied ABA have been limited by rapid metabolism of the hormone in the plant.

In plants, the predominant pathway (see below) of metabolism of (+)-ABA involves hydroxylation at the 8' position affording 8'-hydroxyABA (2) which undergoes cyclization by attack of the 8'-hydroxyl group onto the enone system producing phaseic acid (PA, 3). The intermediate hydroxylated ABA compound 2 has rarely been found in plant extracts, most probably because it readily cyclizes during manipulation. Phaseic acid (3) the more readily isolable ABA catabolite, has little or no activity in most assays.

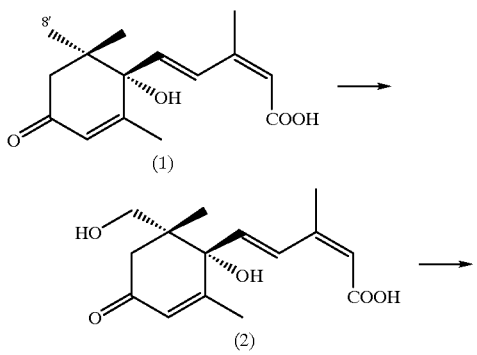

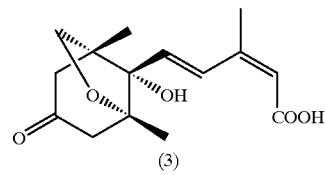

2. Description of the Prior Art

Recently, new ABA analogs bearing a methoxy group on either the 8' or 9'-carbon atom have been synthesized and tested by Hirai's group in Japan (Y. Todokori, N. Hirai and K. Koshimuzuz. 8' and 9'-methoxyabscisic acids as antimetabolic analogs of abscisic acid Biosci. Biotech. Biochem 1994 58: 707–715); S. Nakano, Y. Todoroki, N. Hirai, and H. Ohigashi. Synthesis and biological activity of 7'-, 8'- and 9'-alkyl analogizes of abscisic acid Biosci. Biotech. Biochem. 1995 59 699–1706). These compounds were found to have potent activity, depending upon the assay. Their results suggest that modifying the geminal dimethyl groups in some instances does not prevent the molecule from being perceived as ABA-like, and the authors postulate that the alterations prevent rapid metabolic breakdown by enzymes that degrade ABA.

However, the syntheses that they used are not practical. Their procedure for the methoxy derivatives takes 15 steps, with one reaction that gives a mixture of double bond isomers, and another that gives a mixture of diastereomers at the 1' and 6'- carbons. The yield of racemic methyl ethers, as a mixture with the trans forms, i.e. four compounds, is calculated from their experimental results to be 0.22%. The alkyl analogs are synthesized by similar routes and overall poor efficiency.

Two groups have synthesized 8'-fluorinated ABA analogs that have potent biological activity (Y. Todoroki, N. Hirai, K. Koshimizu. 8', 8' difluoro- and 8',8', 8'- trifluoroabscisic acids as highly potent long lasting analogues of abscisic acid Phytochem. 1995 38: 561–568. B. T. Kim, Y. K. Min, T. Asami, N. K Park, I. H. Jeong, K. Y. Cho and S. Yoshida. Synthesis and biological activities of new fluorinated abscisic acid. Bioorganic and Medicinal Chem. Lett. 1995 5 275–278). In both cases the syntheses are lengthy and not practical for plant growth regulator applications.

SUMMARY OF THE INVENTION

It is an object of the present invention to develop potent biologically stable ABA analogs that can be used to prolong ABA effects in plants for agricultural and basic research applications.

It is another object of the present invention to alter the 8'- or the 9'-carbon atom of ABA to develop analogs that are resistant to enzymatic oxidation (probably involving cytochrome P-450 monooxygenases) but retain or provide an enhancement to the bioactivity of the natural hormone.

According to one aspect of the invention a compound of structural formula I

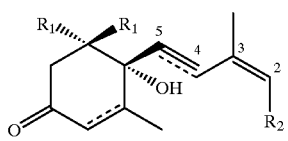

is provided wherein one of $R_1$ is alkenyl, alkynyl, aryl, cycloalkenyl, other further substituted carbon chain including deuterium containing residues, and carbon containing substituents with heteroatoms and halogens and the other is methyl, and wherein the five member carbon side chain includes a methyl group at C3, with C5 attached to the ring as shown, including a trans double bond at the C4–C5 position, or a triple bond at this position, and either a cis or a trans double bond at the C2–C3 position, and $R_2$ is $CH_2OH$, CHO, COOH, COO alkyl, or derivatives thereof, and wherein the cyclohexanone ring double bond may also be reduced.

According to another aspect of the invention, a new class of 8'-abscisic acid (ABA) analogs is provided of the structural formula Ia

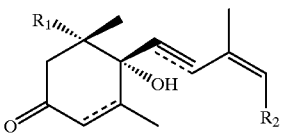

wherein, $R_1$ is alkenyl, alkynyl, aryl, cycloalkenyl, other further substituted carbon chain, including deuterium containing residues, and carbon containing substituents with heteroatoms and halogens; and wherein the five member carbon side chain includes a methyl group at C3, with C5 attached to the ring as shown, including a trans double bond at the C4–C5 position or a triple bond at this position, and either a cis or a trans double bond at the C2–C3 position, and $R_2$ is $CH_2OH$, CHO, COOH, COO alkyl, or derivatives thereof and wherein the cyclohexanone ring double bond may also be reduced.

According to another aspect of the invention, a new class of 9'-abscisic acid(ABA) analogs is provided, of structural formula Ib

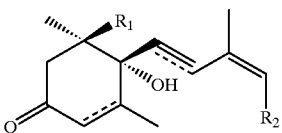

wherein, $R_1$ and $R_2$ are as defined above for formula Ia.

According to another aspect of the invention, a novel process is provided for the synthesis of 8'-ABA analogs. See general reaction schemes A and B, below.

When 8'-analogs are required, the overall process involves reaction of 2,6-dimethylcyclohexa-2,5-dien-1,4-dione, or derivative such as the ketal at C4, with the dianion of 3-methyipent-2-en-4-yn-1-ol or hydroxyl protected derivative. Conjugate addition of the unsaturated group to the enone is carried out with a Grignard reagent. Oxidation of the C1 hydroxyl group to a functional derivative e.g. the acid, ester, acid chloride, etc. is accomplished with standard methods. The C4–C5 triple bond can be reduced to the trans double bond with a hydride reducing agent e.g. a suitable hydride.

Although our assays were performed on optically pure materials to compare with natural ABA, it will be appreciated that where racemic materials are employed, a resolution step will be required.

Preparation of acetylenic analogs at C4–C5 is most effective using the non-ketalized quinone (scheme A below) in the following manner. The dianion of 3-methylpent-2-en-4-yn-1-ol is generated in THF at −78° to −20° C. by addition of two equivalents of n-butyllithium. This is added to a solution of one equivalent of the quinone in THF at −100° C. in the presence of tetramethylethylene diamine. This reaction selectively adds the sidechain to the more hindered carbonyl. Further addition of a Grignard reagent ($R_1MgX$, where X=Cl, Br or I) to this reaction will add an $R_1$ group to the 8' position, giving the 8'-substituted keto-diol in one pot.

Preparation of analogs with a trans double bond at C4–C5 is best carried out from the ketal (scheme B below) under the following conditions. The dianion of 3-methylpent-2-en-4-yn-1-ol is generated in THF at −78° to −20° C. by addition of two equivalents of n-butyllithium. To this is added 1 equivalent of the ketalized quinone. After the reaction is complete, reduction of the triple bond can be carried out in situ by addition of Red-Al at 0° C. The ketal can be removed using 10% HCl in TBF at 0° C. Conjugate addition of an R group is carried out through reaction with a copper mediated Grignard reagent. The dianion of the keto-diol is first generated at −78° to −20° C. with either methyllithium, lithium diisopropyl amide or sodium hydride, and then transferred to a solution of copper iodide and $R_1MgX$ (X=Br, Cl or I) at −78° to −20° C.

Oxidation of the C1 hydroxyl group to the acid is accomplished with standard methods.

Further modification of the 8'-position can be carried out through selective ozonolysis, and subsequent Wittig-type reactions onto the formed aldehyde, of 8'-methylene ABA.

Some reactions can be combined to shorten the synthesis.

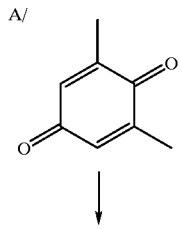

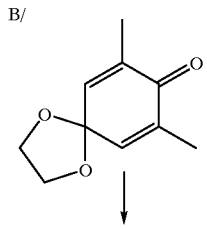

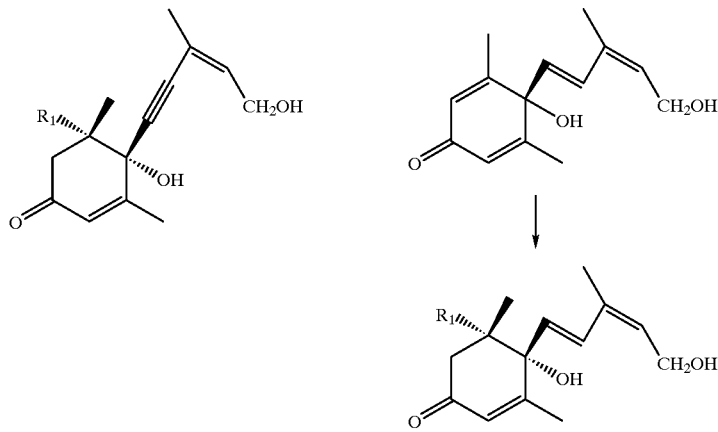
For Example, $R_1$=$CH_2CCH$, $C{\equiv}CH$, $CH_2CH{=}CH_2$, $CH{=}CH_2$.
The following more detailed reaction schemes (i) to (iv), further illustrate the process of scheme B/.
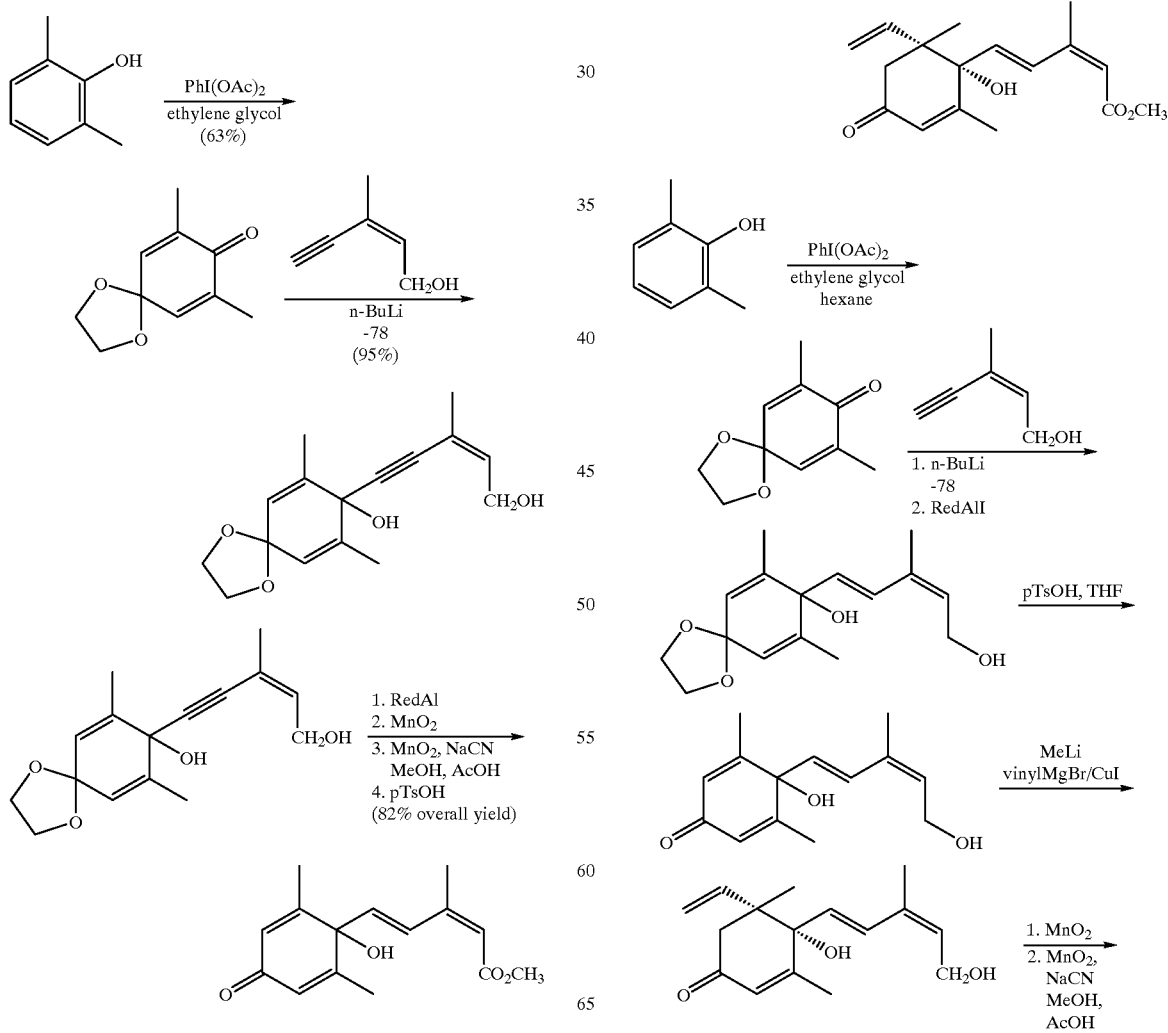

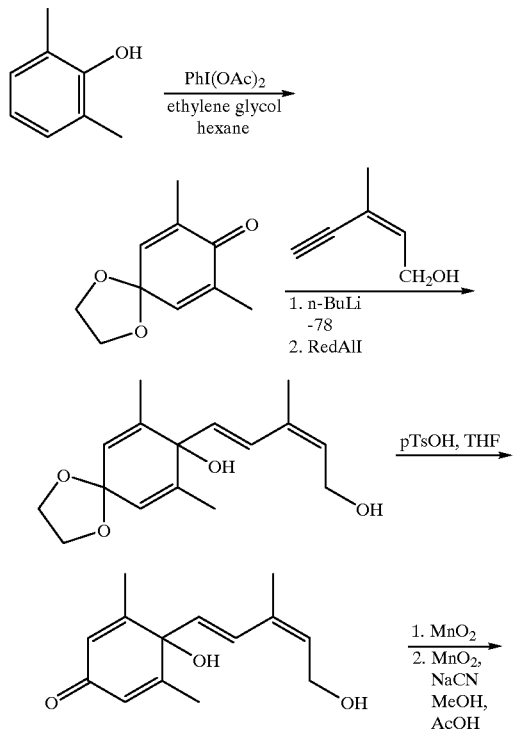
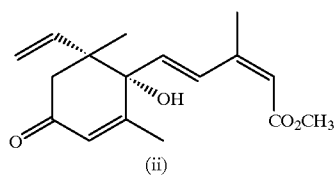
The following is a more detailed reaction scheme (v), further illustrating the process of scheme A/.
(v)

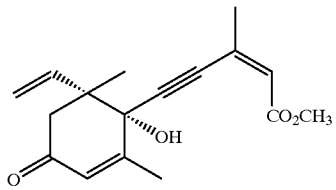

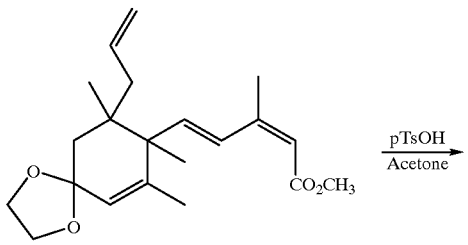

The 9'-analogs of formula Ib can be synthesized by alkylation of 2,6-dimethyl4,4-ethylenedioxycyclohex-2-enone with allyl iodide. Subsequent reaction of the product with the dianion of 3-methyl-pent-2-en-4-yn-1-ol affords a 1:1 mixture of the 8'- and 9'-substituted acetylenic ABA analogs. Reduction of the C4–C5 triple bond to the trans double bond and oxidation of the C1 carbon hydroxyl group to the appropriate level (e.g. to the acid) is accomplished by standard methods. The 8'- and 9'-allyl esters can be separated by HPLC using a column with a chiral support (Daicel Chiralcel-OD).

The following is a more detailed reaction scheme C/ for the synthesis of 9'-analogs.

C/

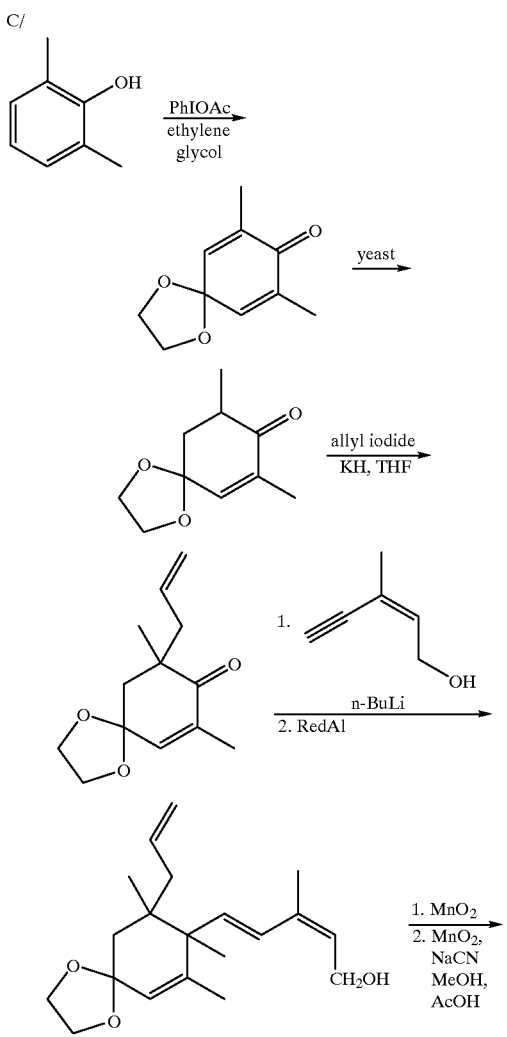

DESCRIPTION OF THE PREFERRED EMBODIMENT(S)

Figure 1:
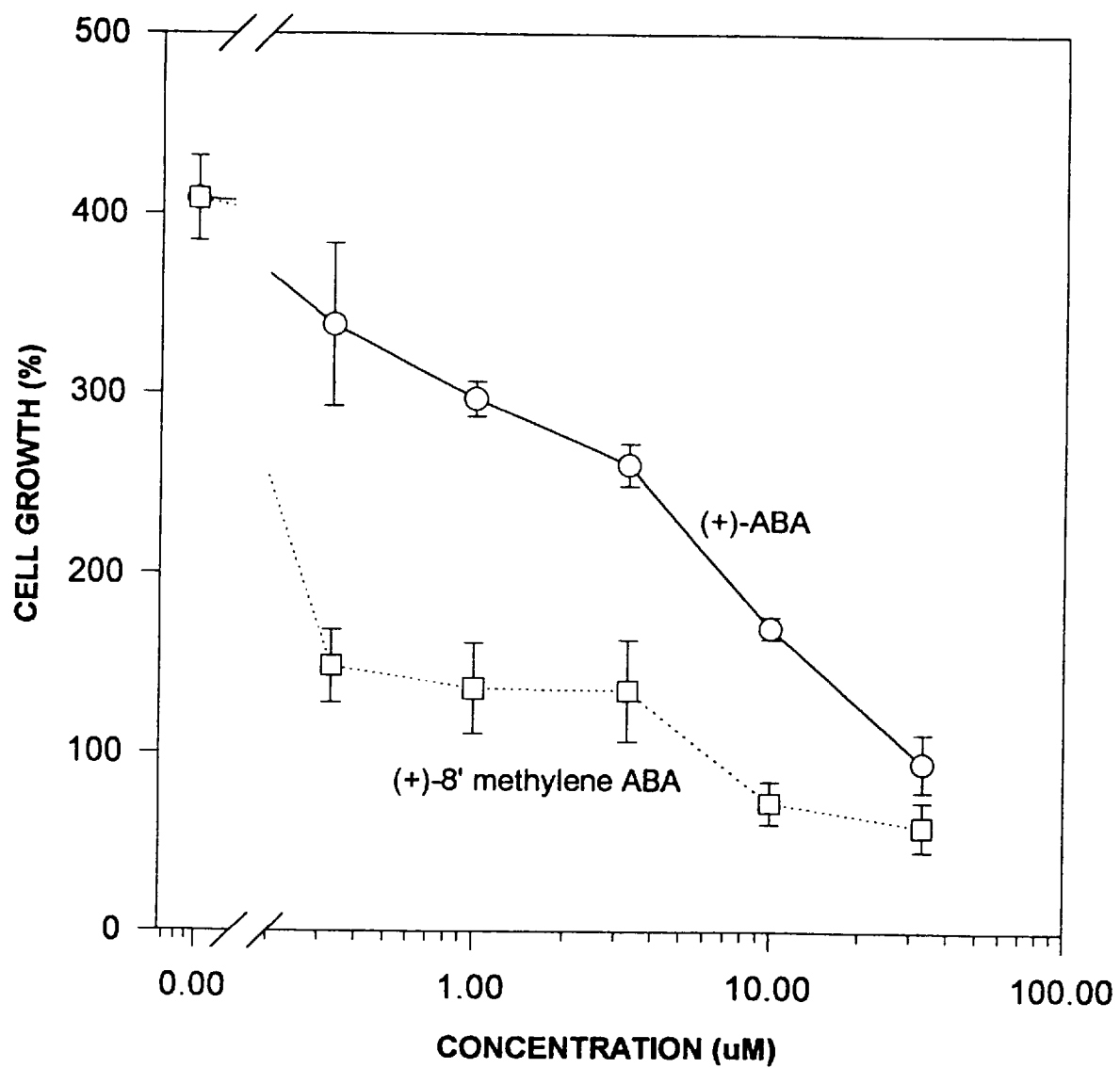
FIG. 1 is a graph which illustrates the growth inhibition dose-response for (+)-ABA and 8' methylene ABA.

The novel ABA analogs are altered at the 8'- or 9'- carbon atom with carbon chains containing unsaturations. The C-8' or 9' methyl group can be replaced for example, by $CH_2=CH$ (methylene), $CH_2CH=CH_2$ (allyl), $C\equiv CH$ (acetylene), $CH_2CCH$ (propargyl) or longer carbon chains with unsaturation, and include cyclic compounds and substituents with heteroatoms.

We have also developed methods of synthesis that are practical and economical, and give numerous biologically active compounds from readily available precursors efficiently.

Results in a number of different assays described in the Examples which follow, show that the new 8'- or 9'-altered analogs have activity comparable or greater than that of the natural hormone. Accordingly, these analogs have potential application in altering any biological process in plants in which ABA is involved.

The 8'-substituted ABA analogs claimed here have alterations to the ABA molecule at the carbon atom that is oxidized in the catabolism of ABA to phaseic acid. Altering the ABA molecule in this fashion renders the hormone analogs more resistant to biological degradation. The analogs with unsaturated chains at the 8'- and 9'-carbon atoms have been found to be more active than saturated versions.

The potential applications for 8'- and 9'-carbon unsaturated substituted ABA analogs for crop improvement are outlined in point form below:

Antitranspirants: reduction of water loss during transplantation or when soil moisture is low or unavailable Promotion of root growth and/or increased root-shoot ratio under drought conditions or during seedling establishment Increasing survival and reducing damage under suboptimal growth conditions, especially due to temperature and other abiotic stresses.

Regulation of germination/dormancy, for example by:
Preventing preharvest sprouting by maintaining dormancy
Enabling fall seeding of spring crops by inhibiting premature germination
Potential herbicidal activity either by preventing weed growth until crops are established or by hormonal toxicity.

Production of seed products, by increasing production of seed proteins and lipids during embryo development, including increased expression of ABA-dependent transgenes.

Production of artificial seed for micropropagation. Facilitating desiccation of somatic embryos and normal development in culture Affinity labeling reagents for identifying proteins involved in ABA action and metabolism An example of the synthetic method and biological activity of new 8'-unsaturated ABAs is given below.

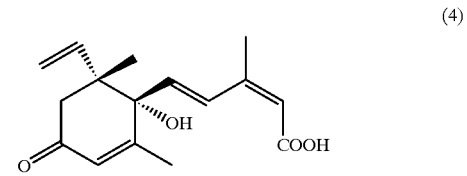

(4)

That is, the analog 8'-methylene ABA is synthesized by copper catalyzed 1,4-conjugate addition of a Grignard reagent ($R_1MgBr$) to a symmetrical cyclohexadienone with a carbon containing sidechain R, as generally shown below.

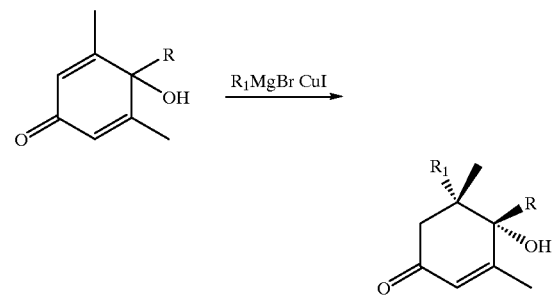

More details of the reactions involved are shown in reaction scheme (v), above.

The starting materials used in the synthesis of the analogs described here were reported by us earlier. (B. Lei, S. R. Abrams, B. Ewan, and L. V. Gusta. 1994. *Phytochem.* 37: 289–96, Achiral cyclohexadienone analogines of abscisic acid: synthesis and biological activity the disclosure of which is incorporated herein by reference).

General Experimental Conditions

Melting points (mp) are uncorrected and recorded on an Ernst Leitz Weltzlar hot stage melting point apparatus. Proton nuclear magnetic resonance ($^1H$ NMR) were recorded on a Bruker AMX-500 spectrometer(500 MHz). Carbon-13 ($^{13}C$ NMR) spectra were recorded on Bruker AMX-500 spectrometer (125 MHz). $CDCl_3$ was used as solvent in all NMR experiments with $CHCl_3$ as reference. Chemical shifts ($\delta$) and coupling constants (J) are reported as if they are first order. High resolution mass spectra (HRMS) were recorded in the electron impact mode using VG 70-250SEQ double-focusing hybrid spectrometer with a Digital PDP 11/73 data system. Flash column chromatography was performed using Merck silica gel 60 (230–400 mesh). The solvent tetrahydrofuran (THF) was dried by distillation from sodium and benzophenone. Unless otherwise indicated, all reactions were conducted under an atmosphere of dry argon.

(±) Methyl 8'-methyleneabscisate

Grignard/CuI solution was prepared by adding vinylmagnesium bromide (Aldrich, 1.0 M in THF, 34 ml, 34 mmol) to CuI (grounded powder, 0.38 g, 2 mmol) at 0° C. The mixture was stirred at 0° C. for 10 min and ready for use. Methyl-(2Z,4E)-5-(2,6-dimethyl-1-hydroxy-4-oxocyclohexa-2,5-dienyl)-3-methylpent-2,4-dienoate PBI-252 (3.60 g, 13.7 mmol) (Lei et al, 1994; vide supra) was dissolved in dry THF (300 ml) and cooled to −78° C. with an external dry ice/acetone bath. MeLi (Aldrich, 1.4 M in THF, 9.7 ml, 13.7 mmol) was added, forming a red solution. The solution was stirred for 15 min and then the prepared Grignard/CuI solution was transferred to it. The resultant dark solution was stirred at −78° C. for 20 min, diluted with ether (200 ml) after removing the dry icelacetone bath, and then quenched with 200 ml of 10:1 saturated $NH_4Cl$/ $20\%NH_4OH$ solution. The mixture was stirred for 20 min and separated. The organic layer was washed with brine (100 ml). The combined aqueous layers were extracted with ether (2×100 ml). The organic layers were combined, dried over anhydrous $MgSO_4$ and concentrated. The residue was purified by column chromatography (25% ethyl acetate/hexane) to give 2.74 g (69%) of product as a solid, Recrystallization from ether/hexane gave white crystals. mp 116–117° C.; $^1H$ NMR: δ7.846 (d, 1H, J=16.0 Hz, H-4), 6.058 (dd, 1H,J= 10.8, 17.6 Hz, H-8'), 6.056 (d, 1H, J=16.0 Hz, H-5), 5.961 (s, 1H, H-3'), 5.734 (s, 1H, H-2), 5.291 (d, 1H, J=10.8 Hz, H-10', cis to H-8'), 5.231 (d, 1H, J=17.6 Hz, H-10', trans to H-8'), 3.679 (s, 3H, OMe), 2.493 (d, 1H, J=17.2 Hz, H-5'), 2.411 (d, 1H, J =17.2 Hz, H-5'), 2.000 (s, 3H, C-6, Me), 1.892 (d, 3H, J=0.9 Hz, C-7', Me), 1.24 (s, 3H, C-9', Me) ppm. $^{13}C$ NMR: δ197.0, 166.3, 163.0, 149.2, 140.7, 134.9, 129.1, 127.3, 118.5, 118.0, 78.2, 51.2, 47.7, 47.5, 21.1, 20.6, 19.2 ppm. HRMS: calcd for $C_{17}H_{22}O_4$ ($M^+$) 290.1518, found 290.1522.

Resolution of (±) Methyl 8'-methyleneabscisate

Resolution was effected by preparative chiral high pressure liquid chromatography (HPLC). A solution of racemic methyl ester in 1:4 2-propanol/hexane (1 ml, approx. 20 mg/ml) was injected onto a Chiralcel OD column (Daicel, 250 mm×10 mm ID, preceded by a Whatman CSK1 HC Pellosil guard column) and eluted with 1:4 2-propanol/hexane at 2 ml/min, with UV detection at 262 nm. Five injections afforded (+) methyl 8'-methyleneabscisate (55 mg), eluting at 14 min and (−) methyl 8'- methyleneabscisate (44 mg), eluting at 23 min. Each isomer was greater than 99% optically pure, as determined by analytical HPLC (Daicel Chiralcel OD 250 mm×4.6 mm ID).

(+) Methyl 8'-methyleneabscisate, $[\alpha]D^{24}$ +386.6° (c=1.3% in $CHCl_3$); mp (ether/hexane) 124–125° C.; $^1H$ NMR: δ7.802 (d, 1H, J=16.1 Hz, H-4), 6.019 (dd, 1H, J=11.0, 17.5 Hz, H-8'), 6.018 (d, 1H, J=16.1 Hz, H-5), 5.918 (d, 1H, J=0.8 Hz, H-3'), 5.692 (s, 1H, H-2), 5.245 (d, 1H, J=11.0 Hz, H-10', cis to H-8'), 5.185 (d, 1H, J=17.5 Hz, H-10', trans to H-8'), 3.635 (s, 3H, OMe), 2.493 (d, 1H J=17.2 Hz, H-5'), 2.411 (d, 1H, J =17.2 Hz, H-5'), 1.958 (s, 3H, C-6, Me), 1.851 (s, 3H, C- 7', Me), 1.081 (s, 3H, C-9', Me) ppm. $^{13}C$ NMR: δ196.9, 166.3, 163.0, 149.2, 140.7, 134.9, 129.1, 127.3, 118.5, 118.0, 78.2, 51.2, 47.7, 47.5, 21.1, 20.6, 19.2 ppm. (−) Methyl 8'-methyleneabscisate, $[\alpha]D^{24}$−386.5°(c=1.7% in $CHCl_3$); mp (ether/hexane) 124–125° C.; $^1H$ and $^{13}C$ NMR spectra identical to those of the (+) enantiomer.

(+) 8'-methyleneabscisic acid (+) Methyl 8'-methyleneABA (23 mg) was dissolved in methanol (7 ml) and 7 ml of 2N NaOH solution was added dropwise. The solution was stirred at room temperature for 4 hr. and concentrated to remove most methanol. The residue was dissolved in 2N NaOH (5 ml) and washed with ether (5 ml). The aqueous layer was acidified with 10% HCl solution and then extracted with ethyl acetate (3×10 ml). The combined ethyl acetate layers were dried over anhydrous $Na_2SO_4$ and evaporated to afford (+) 8'-methyleneABA (21.3 mg 97%) as a solid. $[\alpha]D^{24}$+351.3° (c=2.3% in $CHCl_3$), $^1H$ NMR: δ7.756 (d, 1H, J=16.1 Hz, H-4), 6.057 (d, 1H, J=16.1 Hz, H-5), 6.027 (dd, 1H, J=11.0, 17.5 Hz, H-8'), 5.938 (s, 1H, H-3'), 5.707 (s, 1H, H-2), 5.231 (d, 1H, J=11.0 Hz, H-10', cis to H-8', 5.171 (d, 1H, J=17.5 Hz, H-10', trans to H-8'), 2.508 (d, 1H, J=17.3 Hz, H-5'), 2.424 (d, 1H, J=17.3 Hz, H-5'), 1.995 (s, 3H, C-6, Me), 1.854 (s, 3H, C-7', Me), 1.090 (s, 3H, C-9', Me) ppm. $^{13}C$ NMR: δ197.3, 170.9, 163.2, 151.5, 140.8, 135.7, 129.2, 127.3, 118.2, 117.8, 78.5, 47.7, 47.3, 21.4, 20.7, 19.3 ppm. HRMS: calcd for $C_{16}H_{22}O_4$ ($M^+$) 276.1362, found 276.1354.

(−) 8'-methyleneabscisic Acid

Hydrolysis of (−) methyl ester (26 mg) with the method as above yielded (−) 8'- methyleneABA (21.5 mg, 87%) as a solid. $[\alpha]D^{24}$ −368.1°(c=2.3% in $CHCl_3$). The $^1H$ and $^{13}C$ NMR spectra were identical with those of the (+) enantiomer.

The addition of the new carbon-containing group proceeds regioselectively affording the new group cis to the hydroxyl group. The structure of the novel analogs and the regiochemistry of the alkylation was proven with an isotopically labelled analog, made by using trideuteromethyl magnesium iodide in the Grignard reaction. The product obtained, after modification of the sidechain by conventional transformations, ABA with one deuteromethyl group in the geminal dimethyl pair, was resolved and the (+)-enantiomer subjected to oxidation by cultured corn cells according to the procedure described in our recent paper (Balsevich et al Plant Physiol 1994 106: 135–142 incorporated herein by reference). The deuterated ABA was converted by the cells to phaseic acid containing two deuterium atoms. This result confirms that the new methyl group is added from the same side as the hydroxyl group.

The method is amenable for the synthesis of numerous 8'-substituted ABA analogs, requiring only a change in the $R_1$ group of the Grignard reagent to give different compounds. The overall conversion is high. For example, for 8'-methylene ABA, the yield from commercially available starting materials is 9.2% and the number of steps is 8, using our current method of synthesis. For analogs having an acetylene and alcohol or aldehyde in the sidechain, the number of steps will be reduced by 2 or 3, with the overall yield increased. The specific examples here are of racemic compounds that are resolved into their optically pure forms, but the method also allows for synthesis of optically active compounds using chiral reagents.

Biological Activity of ABA Analogs with 8'-carbon Substituents

The 8'-substituted ABA analogs are active in a wide range of assays for ABA. The novel analogs appear to be recognized by plants in a manner similar to the natural hormone. The important feature of these analogs is that the substitution to the molecule leaves intact the important functional groups of the ABA molecule. This may account for the broad activity observed with these analogs. As an example of the range of ABA effects observed for these analogs, assay results for the (+)-enantiomer of 8'-methylene ABA, compared to that for ABA are given below:

Growth Inhibition of Corn Cells and pH Changes in Corn Cell Medium

Natural ABA causes growth inhibition (Balsevich et al 1994, Plant Physiol. 106: 135–142). FIG. 1 shows the growth inhibition experimental results using suspension-cultured corn cells (var. Black Mexican Sweet). The y-axis shows cell growth (wet weight) expressed as a percentage of the initial weight four days after addition of either natural ABA or the corresponding 8'-methylene derivative. The concentrations are shown on the x-axis. Growth measurements at each concentration were performed in triplicate (as Balsevich et al 1994 Plant Physiol. 106: 135–142) and the average value and standard deviation are shown. The concentration required for 50% inhibition of growth was less than 0.33 $\mu$M of the 8'-methylene ABA and approximately 10 $\mu$M for natural ABA. This is the strongest growth inhibition produced by any ABA analog so far. Over 40 compounds have been tested in this assay.

Figure 2:
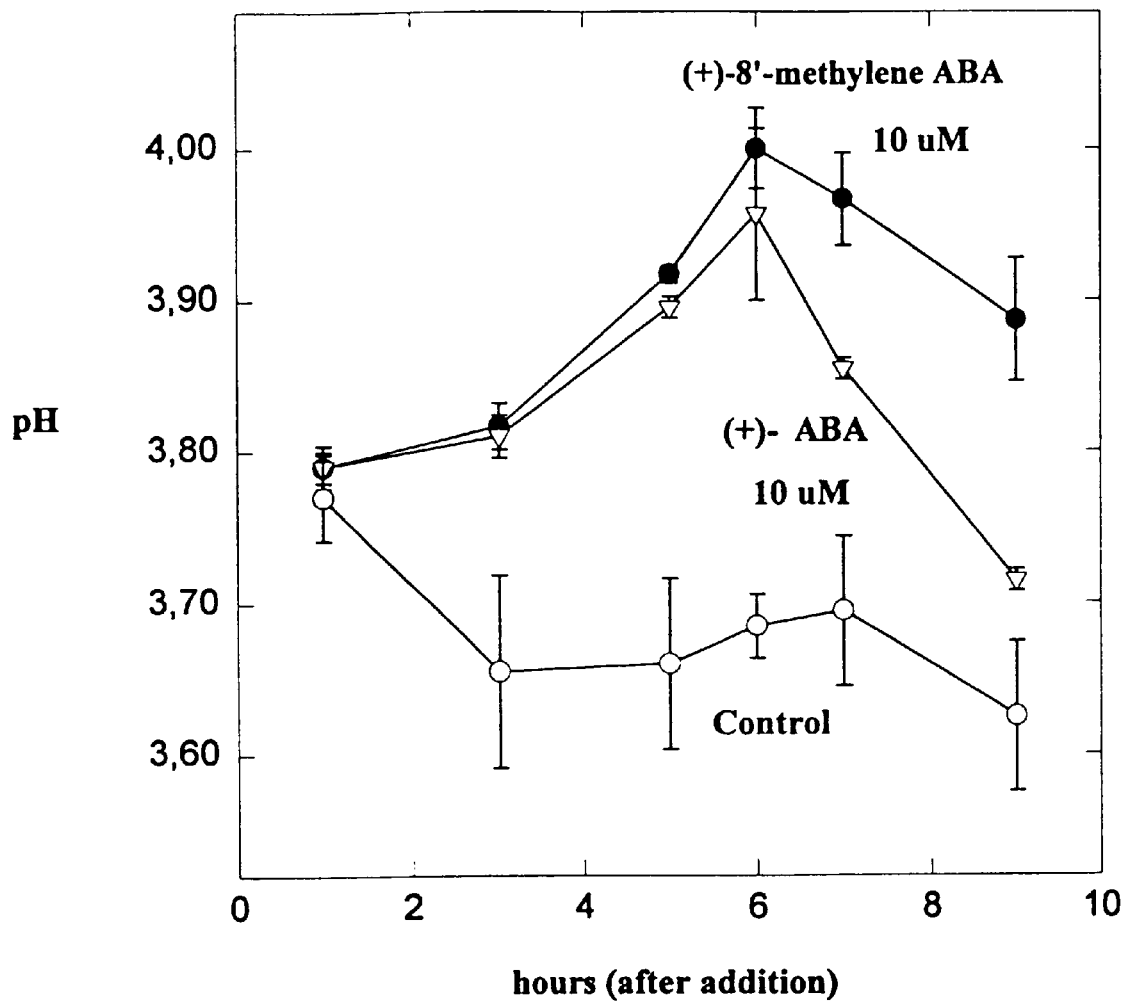
FIG. 2 is a graph which illustrates the effect of (+)-8'-methylene ABA and (+)-ABA on medium pH of BMS Cell Suspension Cultures.

Natural ABA causes a shift in the pH of the medium of cultured corn cells (Balsevich et al 1994, Plant Physiol. 106: 135–142). FIG. 2 shows the effect of 10 $\mu$M solution of (+)-8'-methylene ABA, compared to the same concentration of natural ABA, on the pH of the medium of suspension-cultured corn cells. The 8'-methylene compound causes as great a shift in pH as ABA.

Transpiration in Wheat Seedlings

Figure 3:
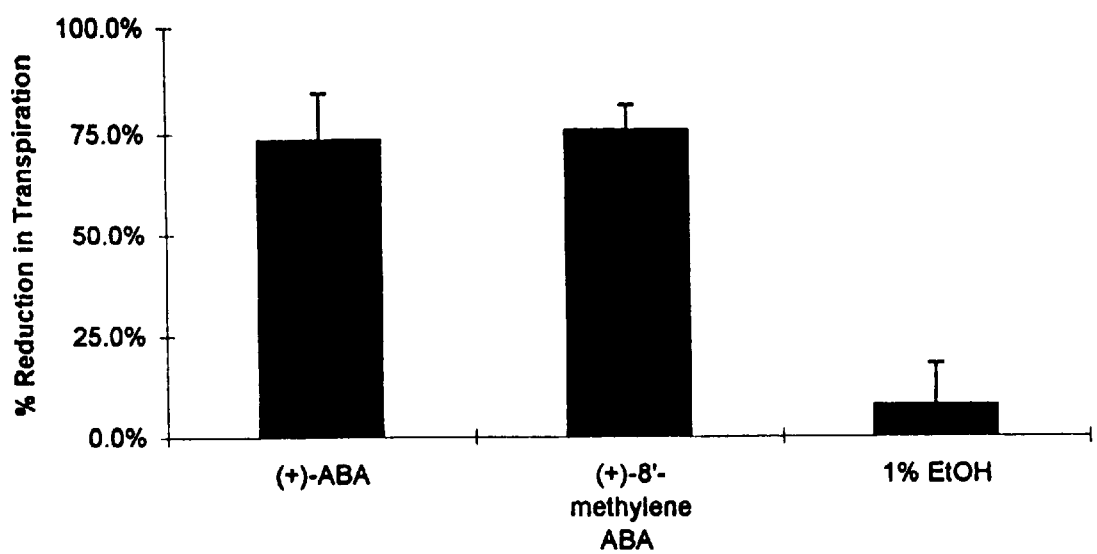
FIG. 3 is a graph which illustrates the reduction in transpiration of wheat seedlings after 3 hours of treatment with (+)-ABA (100μM) and (+)-8'-methylene ABA (125μM)
Figure 4:
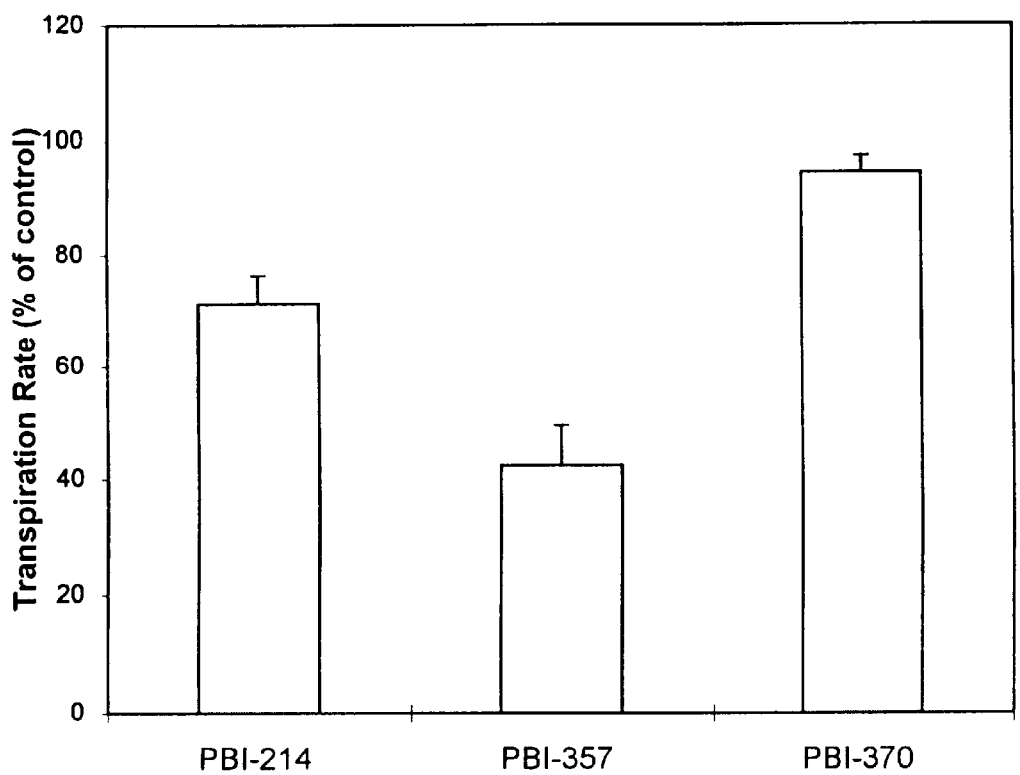
FIG. 4 is a graph which illustrates the transpiration effects of several ABA analogs on wheat seedlings (3 hours after treatment with 10μM analog)

ABA is a key signal molecule involved in regulating transpiration in plants (W. J. Davies T. A. Mansfield 1988 Abscisic acid and drought resistance in plants ISI Atlas of Science: Animal and Plant Sciences 0894–3761 p. 263–269). FIG. 3 shows the effect of natural ABA and (+)-8'-methylene ABA on reduction of transpiration in wheat seedlings. Solutions of 125 $\mu$M were applied to the roots of seedlings and percentage transpiration reduction determined after three hours of treatment. The analog with the saturated 8'-side chain is not as active as the vinyl analog. This difference in activity is shown in FIG. 4 in which the % transpiration effected by the (+)-forms of methyl esters of ABA (214), 8'-methyl (370) and 8'-methylene ABA (357) are compared. The structures are as follows:

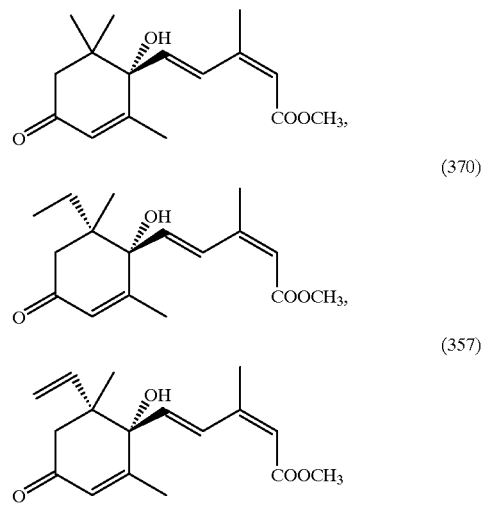

Seed Germination

Figure 5:
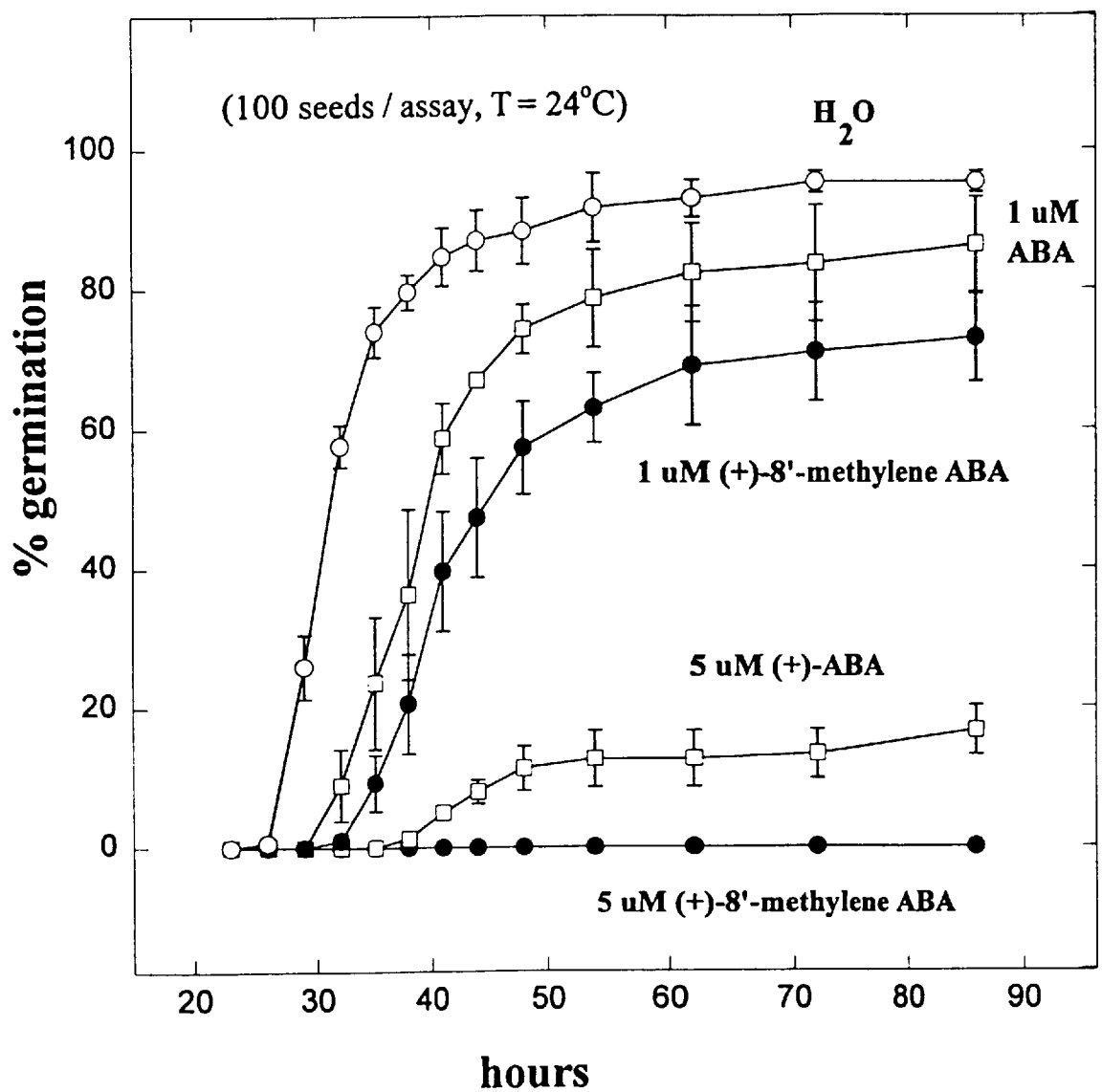
FIG. 5 is a graph which illustrates the effect of (+)-8'-methylene ABA and natural ABA on the germination of cress seed.

ABA inhibits germination of seeds (for example, see L. V Gusta, B. Ewan, M. J. T. Reaney and S. R. Abrams 1992 The effects of abscisic acid metabolites on the germination of cress seed Can. J. Bot. 70: 1550–1555). FIG. 5 shows the effect of (+)- 8'-methylene ABA and natural ABA on germination of cress seed. At 1 $\mu$M the 8'-methylene analog is more potent than ABA, and at 5 $\mu$M while the ABA-treated seed begins to germinate, the seed imbibed with the analog at the same concentration does not germinate. The experimental conditions were as follows: 100 seeds are placed on a 9 cm Whatman no. 1 filter paper in a petri dish and treated with 5 ml of solution.

ABA-Inducible Gene Expression

Figure 6:
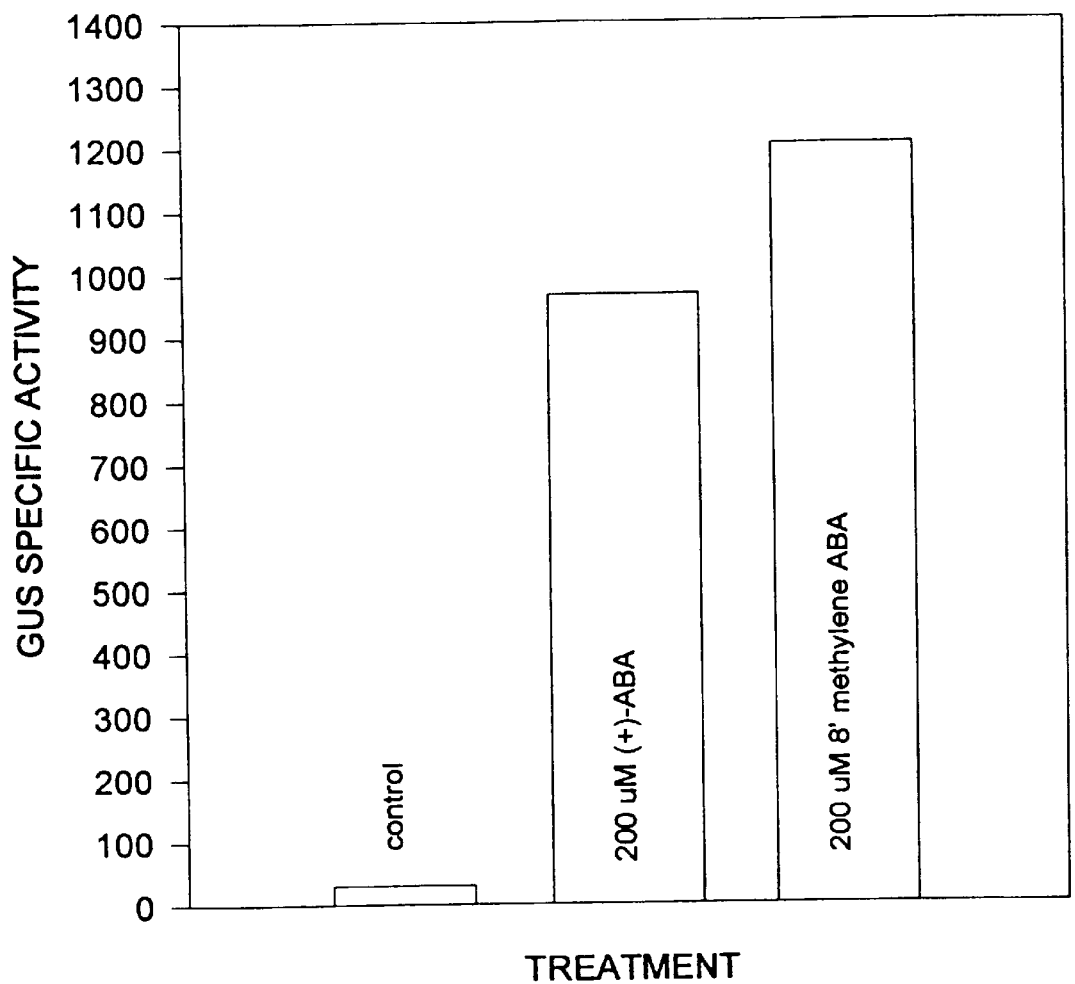
FIG. 6 is a graph which illustrates the induction of β-glucuronidase (GUS) activity in transgenic tobacco plants.

FIG. 6 shows the induction of $\beta$-glucuronidase (GUS) activity in transgenic tobacco seedlings that were imbibed with 200 micromolar ABA or (+)-8'-methylene ABA for 24 hours. The transgenic seedlings contained the ABA-responsive cor6.6 promoter from *Arabidopsis thaliana* (Wang et al 1994, Plant Physiol. 104: 291–292 incorporated herein by reference) fused to the coding sequence of GUS. The ABA-inducibility and other properties of transgenic plants containing this construct have been described (Wang et al 1995 Plant Mol. Biol., 28: 605–617 incorporated herein by reference). The y-axis shows GUS specific activity (extraction and assay performed as described by Jefferson, 1987, Plant Mol. Biol. Reporter 5: 387–405 incorporated herein by reference) in arbitrary units. The results shown are an average of duplicate assays on samples containing 34 seedlings. Both treatments strongly induced GUS activity relative to the untreated control.

Biological Activity of ABA Analog with 9'-Allyl Substituent (9'-ethylene ABA)

Growth Inhibition

Figure 7:
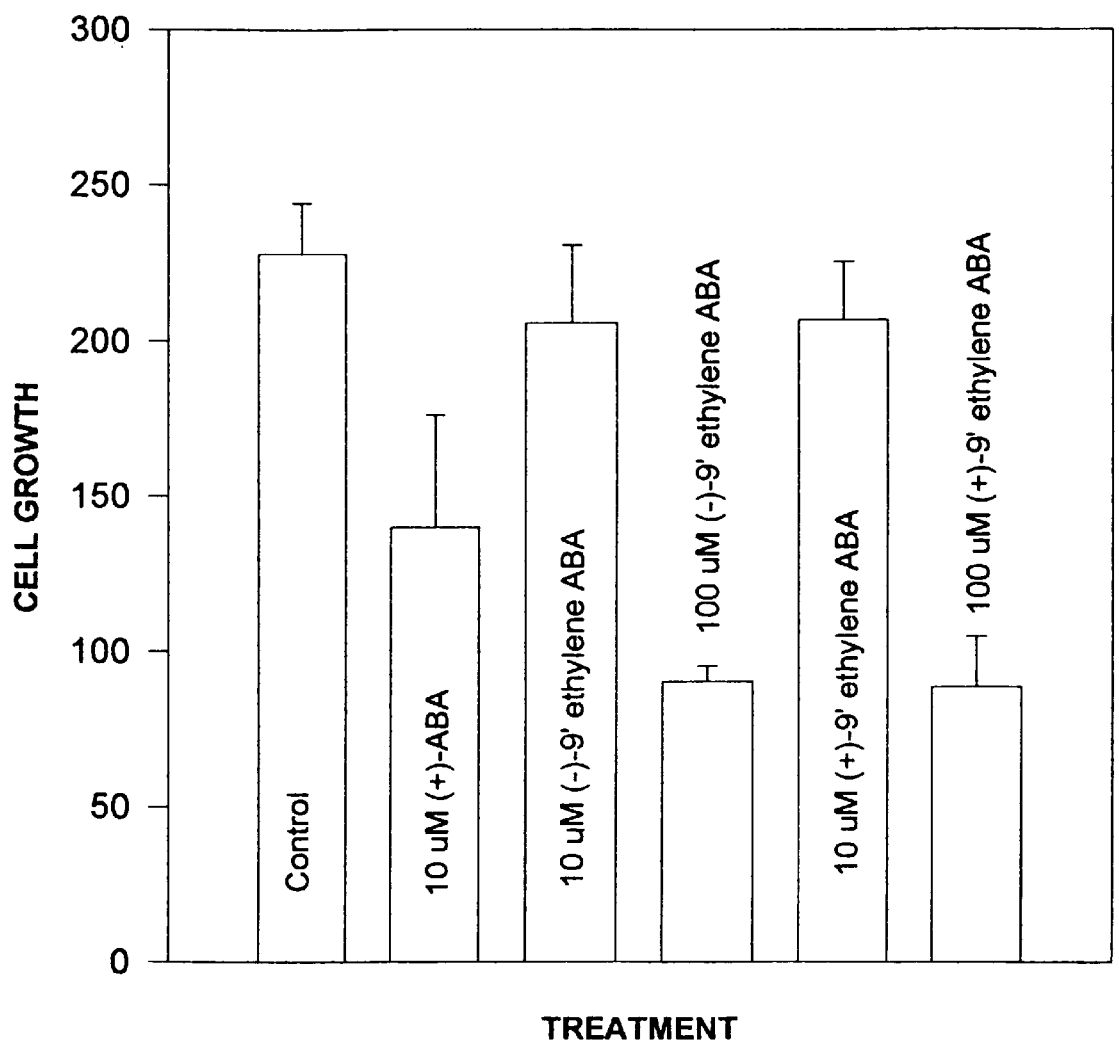
FIG. 7 is a graph which illustrates the growth inhibition of (+)-ABA and 9' derivatives.

The growth inhibitory properties of the two isomers of 9'-ethylene ABA (R1=allyl) are shown in FIG. 7. The assays are performed as described in FIG. 1. Both isomers were inactive at 10 micromolar, and showed comparable activity at 100 micromolar. Although weaker inhibitors than ABA, they retained strong activity.

Transpiration

Figure 8:
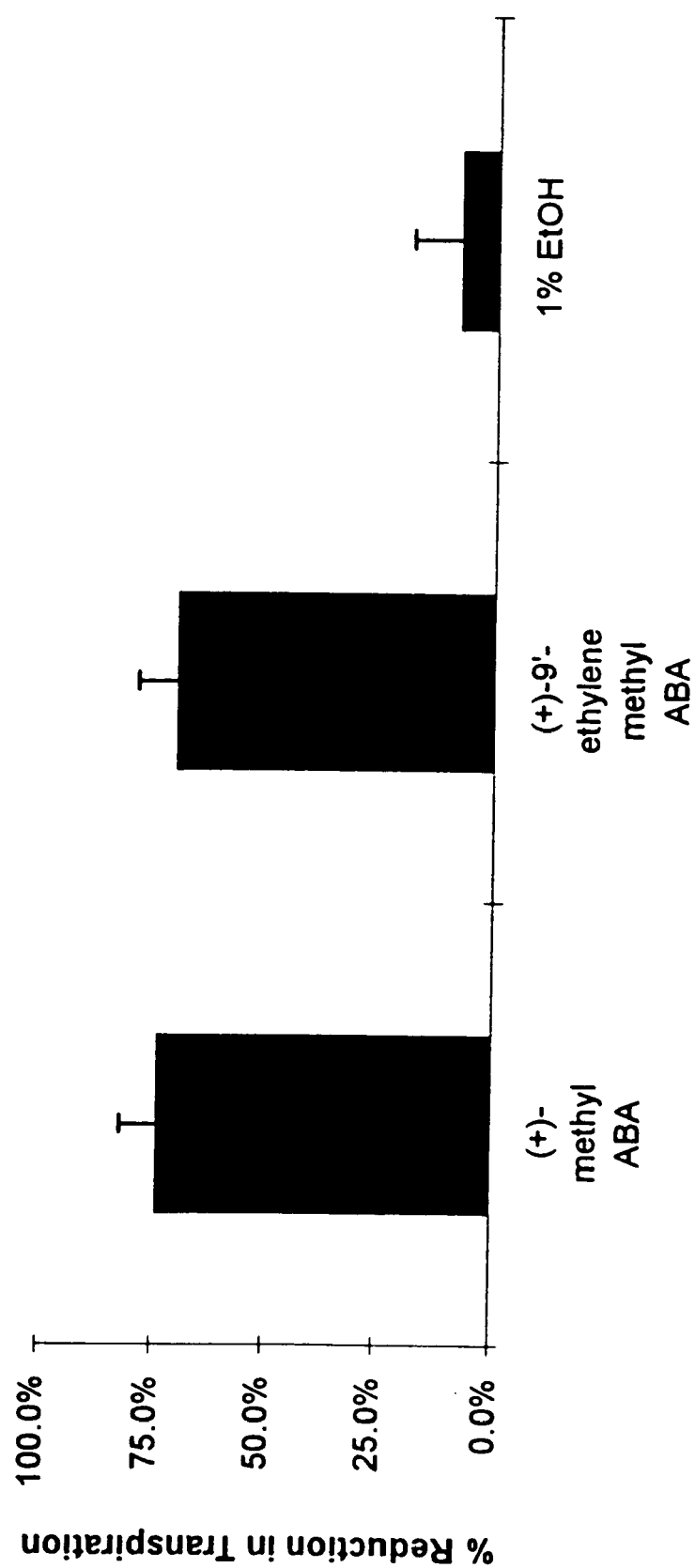
FIG. 8 is a graph which illustrates the reduction in transpiration of wheat seedlings after 3 hours of treatment with (+)-methyl ABA (100μM) and (+)-9'-ethylene methyl ABA (100μM)

In FIG. 8, the results for reduction in transpiration effected by the (+)- forms of methyl esters of ABA and 9'-ethylene ABA are displayed. Equivalent high activity is observed for both compounds.

To be useful, ABA analogs must maintain the ability to act as hormone agonists. The steric hindrance of the additional carbon must not prevent binding to the hormone receptor protein. Encouragingly, there is evidence that the binding of ABA to the receptor and to the hydroxylase are primarily dependent upon different structural features of the ABA molecule. Comparison of the relative importance of the 7', 8', and 9' methyl groups of ABA in inhibiting wheat embryo germination indicated that the presence of the 7' methyl group is absolutely essential but that the others are less crucial (Walker-Simmons[1], et al, 1994). This would suggest that there might be some latitude to alter the substrate binding site (8' carbon) without affecting the part of the molecule critical for receptor binding (7' carbon). ABA analogs bearing a methoxy or alkyl group on either the 8' or 9'-carbon atom (Todoroki et al.[2], 1994; Nakano et al.[3], 1995) or fluorines on the 8'-carbon atom (Todoroki et al.[4], 1995; Kim et al[5], 1995) are strong ABA agonists, suggesting that modifying the geminal dimethyl groups on some instances does not hinder recognition of the molecule as ABA-like. Similarly, alkyl substitutions at the 7', 8' and 9' positions revealed that high hormonal activity was generally maintained for molecules with the same absolute stereochemistry as (+)-ABA (Nakano et al.[3], 1995). In the course of these studies Nakano et al.[3], (1995) showed that (+)-8'-methyl ABA was nearly as active as (+)-ABA in blocking $GA_3$ stimulated $\alpha$-amylase activity, and was more active than (+)-ABA in lettuce seed germination inhibition, stomatal opening of spiderwort and elongation of rice seedling leaves. The high activity of 8'-methyl ABA suggested that the methylene analog (of similar steric bulk) ought also to be recognized as ABA-like. This also means that comparison of the biological activities of 8'-methyl and 8'-methylene ABA would be of considerable interest since, although they are similar molecules, only 8' methylene ABA has the potential to inactivate the 8' hydroxylase irreversibly.

An important criterion in our chemical studies is that the analogs can be synthesized in short, efficient sequences to provide sufficient quantities of material for extensive testing of physiological activity and for further modification at the 8'-position. We show hereinafter that (+)-8'-methylene ABA is more effective than ABA in several biological assays including inhibiting germination in cress and wheat, inhibiting growth of corn suspension cells and reducing transpiration in wheat seedlings.

Synthesis of (+)-8'-methyl ABA (7) (±)-Methyl 8'-methylabscisate was synthesized using the same procedure as for (±) methyl 8'-methylene abscisate by substituting ethylmagnesium bromide for the vinylmagnesium bromide. The two enantiomers of (±)-methyl 8'-methyl abscisate were separated by chiral HPLC and the esters hydrolyzed to the corresponding acids in the same manner as for (+)-8'-methylene abscisic acid. Spectral properties of both acids and esters agreed with those previously reported (Nakano et al.[3], 1995).

(7)

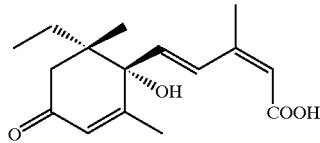

Metabolites of (+)-8'-Methylene ABA [(+)-4] from Maize Suspension Cells

Eighteen g of Black Mexican Sweet maize cells were subcultured into a 1L flask containing 500 ml sterile medium as described previously (Balsevich et al.[6], 1994). The following day, 13.5 mg of (+)-8'-methylene ABA, dissolved in 0.5 ml of ethanol, was introduced to the medium at a final concentration of 100 μM, The culture was incubated at room temperature on a rotary shaker at 150 rpm for 90 h, at which time, HPLC analysis showed a high concentration of metabolite. At the end of the culture period, the cells were removed by filtration. The filtrate was frozen until processed for isolation.

The metabolites were extracted from the culture filtrate by a chromatographic procedure using Supelco Amberlite XAD-2 resin (Balsevich et al. 6, 1994). The crude product isolated from the resin was partially purified by preparative TLC (silica gel 60 $GF_{254}$, 20 cm×20 cm×1 mm, toluene-EtOAc-HOAc 25:15:2 as eluent), giving two isomeric acids, The acids were separately reacted with diazomethane, and then further purified by HPLC as their methyl esters yielding approx. 0.5 mg of each metabolite. Spectral data indicated that the metabolites were two isomeric epoxides.

Metabolite 1: methyl ester of methyl 8'-methyleneoxide ABA 5/6. FTIR (neat) $v_{max}$ $cm^{-1}$: 3446 (O-H), 1717 (C=O, ester), 1654 (C=O, enone), HREIMS: [M+1]$^+$ at m/z 307.1573 ($C_{17}H_{23}O_5$ requires 307.1545); $^1$H NMR: δ7.89 (d, J=16 Hz, 1H-4), 6.01 (d, J=15.9 Hz, 1H-5), 6.00 (s, 1H-3'), 5.74 (s, 3H-2), 3.69 (s, 3H, $CO_2CH_3$), 3.30 (t, J=3.0 Hz, 1H-8'), 3.04 (s, 1H, OH), 2.67 (t, J=4.2 Hz, 1H-10'), 2.61 (dd, J=3.0, 4.1 Hz, 1H-10'), 2.48 (d, J=17.9 Hz, 1H-5'), 2.33 (d, J=17.8 Hz, 1H-5'), 1.99 (s, 5H-6,7'), 0.91 (s, 3H-9').

Metabolite 2: methyl ester of 8'-methyleneoxide ABA 5/6. FTIR (neat) $v_{max\ cm}^{-1}$: 3447 (O-H), 1717 (C=O, ester), 1654 (C=O, enone), HREIMS: [M+1]$^+$ at m/z 307.1560 ($C_{17}H_{23}O_5$ requires 307.1545); $^1$H NMR: δ7.87 (d, J=16.1 Hz, 1H-4), 6.0 (d, J=16.1 Hz, 1H-5), 5.99 (d, J=1.2 Hz, 1H-5), 5.76 (s, 1H-2), 3.69 (s, 3H, $CO_2CH_3$), 3.23 (dd, J-4.0, 3.1 Hz, 1H-8'), 2.77 (s, 1H, OH), 2.74 (t, J=4.1 Hz, 1H- 10'), 2.69 (t, J=3.0 Hz, 1H-10'), 2.34 (s, 2H-5'), 1.99 (d, J=1.0 Hz, 3H-6/7'), 1.94 (d, J=1.1 Hz, 3H-6/7'), 1.02 (s, 3H-9').

(5/6)

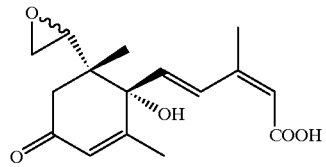

Comparison of depletion of (+)-8-methylene ABA, (+)-8'-methyl ABA and (+)-ABA from corn cell culture media Ethanolic stock solutions of (+)-ABA, (+)-8'-methylene ABA and (+)-8'-methyl ABA were added to flasks containing 0.2 g of corn cells and 10 ml of culture medium to obtain a final concentration of 100 μM of hormone or analog. Aliquots of medium (100 μl) were removed at intervals and analyzed for ABA or ABA analog content by HPLC as described previously (Balsevich et al.[6], 1994). Each compound was inoculated into 3 flasks and duplicate samples were removed at the indicated time points. The corn cells were used 1 or 2 days after subculturing.

Bioassays of (+)-8'-methylene ABA [(+)-4]

Growth Inhibition of Corn Cells and pH Effects

Cell growth was measured by the change in fresh weight over a 4-day period, as previously described (Balsevich et al.[6], 1994). The medium pH changes associated with addition of (+)-ABA and (+)-8'-methylene ABA were also measured as described by Balsevich et al.[6], (1994).

Transpiration in Wheat Seedlings

The transpiration rate of 6 to 10 day old wheat seedlings (Triticum aestivum L. cv Katepwa) was measured as previously described (Rose et al.[7], 1996 incorporated herein by reference). Antitranspirant activity of the analogs (prepared as a 1% ethanol solution in water) was measured over a range of concentrations to determine the concentration where the transpiration rate of the wheat seedling is reduced by 50%. The transpiration rate (μMol $H_2O/cm^2s$) was calculated and then given as a percentage of the initial transpiration rate of the plant (typically 0.28–0.35 μMol $H_2O/cm^2s$), corrected for the effect of the control (1% ethanol).

Cress Seed Germination

Cress seed germination inhibition studies were performed as described by Gusta et al, (1992) except that the experiments were carried out at 23° C. instead of 25° C. and ethanol was used in place of acetone to dissolve the analogs. The final concentration of the ethanol in the assay solutions was <0.05%. Assays were conducted with 100 seeds in each Petri dish and performed in triplicate. The germination measurements were based on the growth of the primary root. A seed was considered germinated when the radical was approximately the same length as the seed.

Wheat Embryo Germination

Grains of soft white wheat (Triticum aestivum L. cv. Clark's Cream) were used. For bioassay, embryos with some adhering endosperm and pericarp attached were cut from the grains with a razor blade. Analogs were prepared by dissolving into a minimal amount of DMSO to prepare a 0.1 M solution, and then diluted with 10 μM Mes, pH 5.8, to 0.01, 0.1, 1, 10 and 100 μM. For each analog concentration six replicate germination assays were conducted on 10 embryos each at 30° C. Embryos were incubated in Petri dishes (100×15 mm) containing 6 ml solution. The number of germinated embryos was counted daily for 4 days and a weighted germination index calculated (Walker-Simmons et al.[8], 1992 incorporated herein by reference).

Gene Expression in Transgenic Tobacco

GUS specific activity in homogenates of cotyledons from homozygous tobacco seedlings containing the transgene Pcor6.6-GUS were measured as described by H. Wang et al.[9] (1995). The results shown are an average of duplicate samples containing cotyledons from 34 seedlings.

In the wheat embryo growth inhibition test, in which both enantiomers of ABA were equally effective, both enantiomers of 4 were compared with (+)-ABA. The 8'-methyl homolog 7 was prepared so that the biological activity of the methylene analog could be compared to the previously reported 8'-methyl ABA (Todoroki et al.[2], 1994).

Metabolism and Persistence of 8'-Methylene ABA in BMS Suspension-Cell Culture

Figure 10:
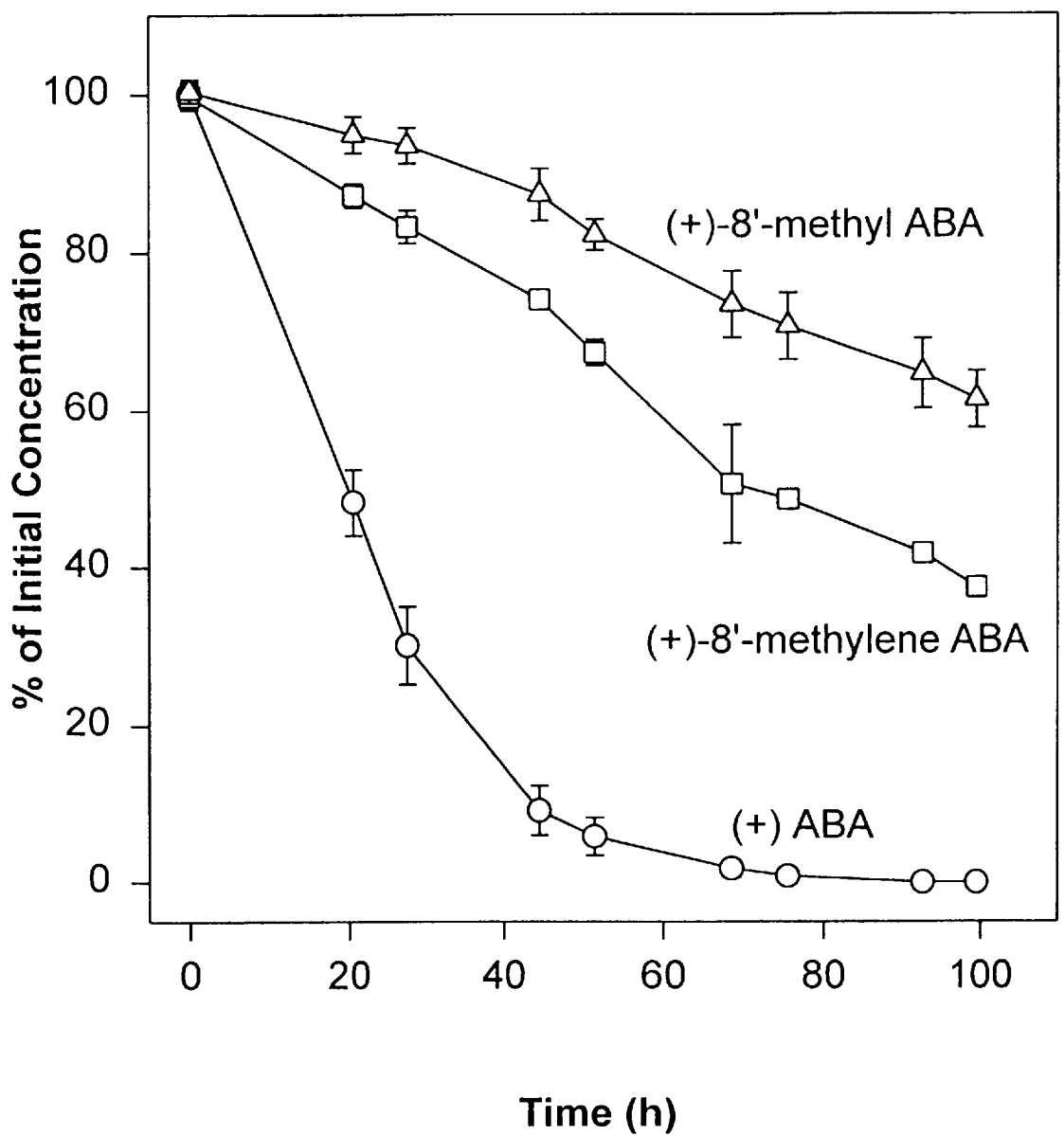
FIG. 10 is a graph which illustrates the time course of the persistence of (+)-ABA, (+)-8'-methylene ABA and (+)-8'-methyl ABA in the medium of maize cell-suspension cultures.

The rates of disappearance of(+)-ABA (1) and (+)-8'-methylene ABA [(+)-4] from the medium were compared to provide a simple estimate of the relative rates of metabolism. As can be seen in FIG. 10, 50% of the (+)-ABA had disappeared from the medium by 24h, whereas the (+)-8'-methylene ABA was only approximately 50% consumed by 100 hours. 8'-Methyl ABA (7) is consumed at a similar rate to the methylene derivative. These experiments show that the 8'-methylene ABA is considerably more persistent than the natural hormone.

In order to assess the stability and pathway of metabolism of *(+)-8'-methylene ABA, the metabolites of (+)-8'-methylene ABA (+)-4 were isolated and identified using the maize suspension cultures in which ABA metabolism has been previously described Balsevich et al.[6], 1994). (+)-8'-Methylene ABA was fed to the cells and two metabolites isolated from the culture medium and were purified as their methyl esters. Mass spectral analysis showed the metabolites each contained one oxygen more than the methyl ester of 8'-methylene ABA. The $^1$H NMR of the two metabolites were very similar, each having lost the signals for the three vinylic protons and each gaining three proton signals with chemical shifts consistent with epoxide formation. The two isomeric epoxides appear to have been formed by oxidation from both faces of the double bond. It is possible that the epoxide oxidation products that cannot cyclize to phaseic acid-like molecules are also active. Further studies are under way to synthesize sufficient quantities of these epoxides to test their biological activities.

Biological Activity of (+)-8'-Methylene ABA in BMS Suspension-Cell Culture

Figure 11:
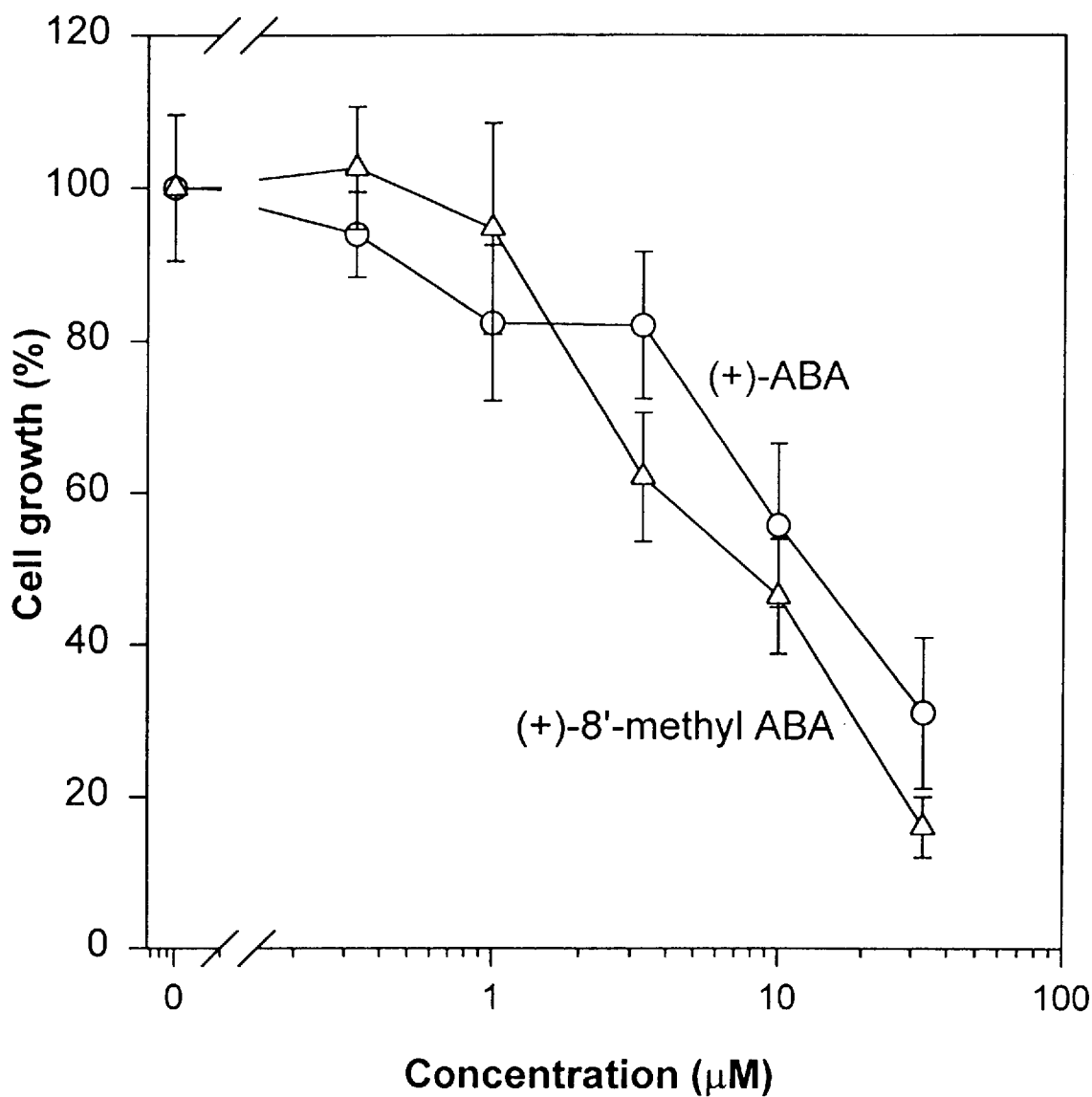
FIG. 11 is a graph which illustrates the effect of (+)-ABA and (+)-8-methyl ABA on corn cell growth.

Corn suspension cultured cells are a well characterized experimental system that has been useful for comparing the biological activity and metabolism of ABA and ABA analogs (Balsevich et al.[6], 1994, Rose et al.[7], 1996). (+)-ABA inhibits growth of maize suspension-cultured cells over a four day period (Balsevich et al. 6, 1994). In this study, (+)-8'-methylene ABA exhibited stronger growth inhibition activity than (+)-ABA at all tested concentrations (FIG. 1). The increased potency of the derivative is more marked at low concentrations. At 0.33 μM, (+)-ABA inhibited growth by 17% relative to the control whereas (+)-8'-methylene ABA produced a 64% reduction. The inhibition caused by 8'-methyl ABA was comparable to that produced by (+)-ABA (FIG. 11). The (+)-methylene ABA is significantly stronger than either (+)-ABA or (+)-8'-methyl ABA. The enhanced activity must be due to more than the simple steric bulk of the extra carbon atom. Since the 8'-methylene and the 8'-methyl analog are depleted from the culture medium at similar rates, the 8'-methylene ABA must have some additional properties, perhaps higher affinity for the receptor.

Natural ABA causes a transient elevation of pH of the corn cell culture medium, reaching a maximum at about 6 h after ABA addition (Balsevich et al.[6], 1994). FIG. 2 shows the effect of 10 μM solution of (+)-8'-methylene ABA, compared to the same concentration of natural ABA, on the pH of the medium of suspension-cultured corn cells. Although the significance of the pH change is not clear, it seems to be an early manifestation of ABA action, which is not produced by PA and only weakly by the unnatural ABA (−)-isomer (Balsevich et al.[6], 1994). The utility of this assay is that it is a relatively rapid test of the inherent hormonal activity of added compounds. The 8'-methylene compound causes a comparable shift in pH as that produced by ABA suggesting that it acts in a similar way.

Biological Activity of 8'-Methylene ABA in Germination Inhibition

Inhibition of Germination of Embryos from Dormant Wheat Grains

Figure 12:
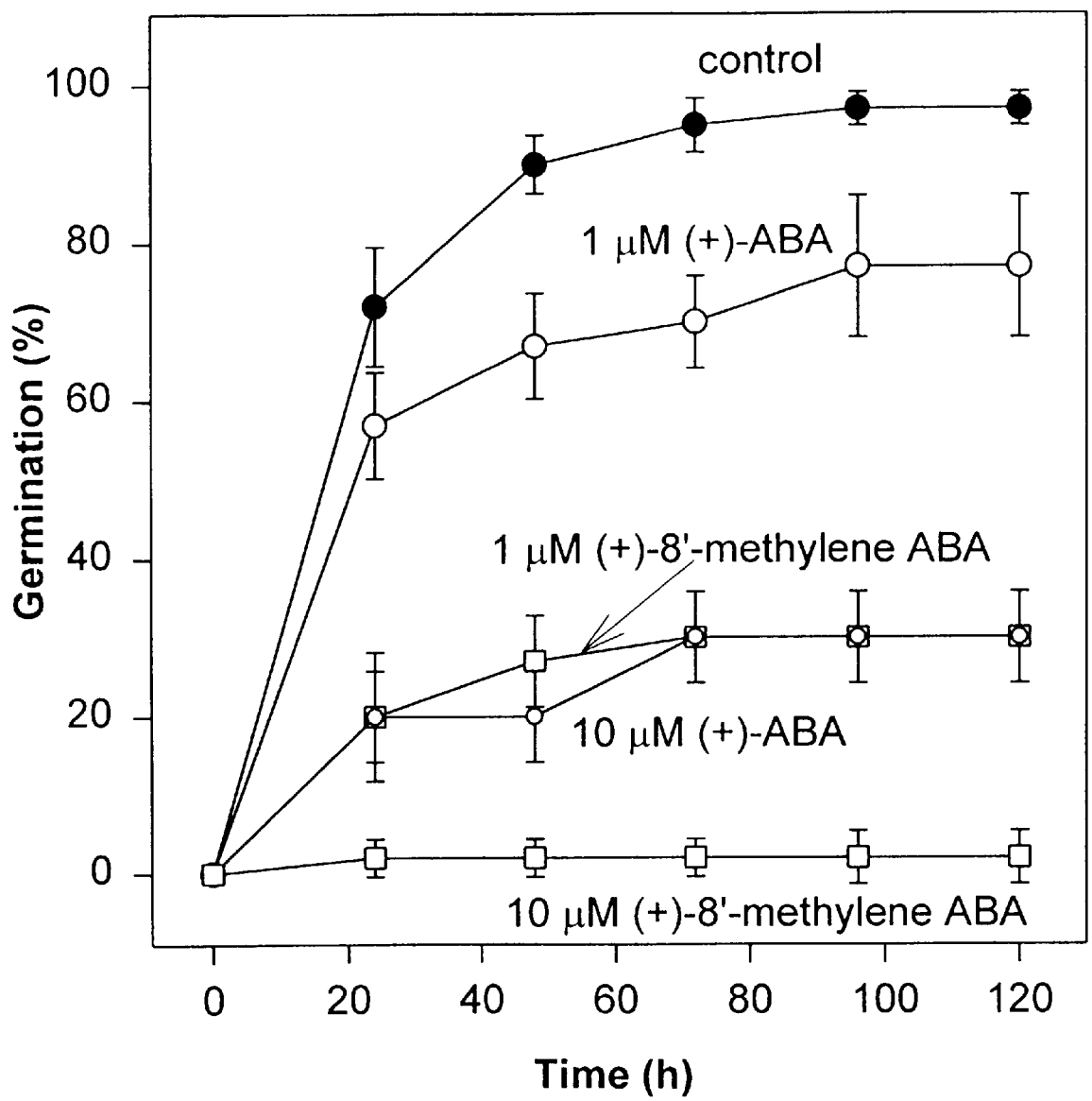
FIG. 12 is a graph which illustrates the biological activity of (+)-ABA and (+)-8'-methylene ABA as germination inhibitors of excised wheat embryos.

Embryos isolated from dormant cereal grains are highly responsive to exogenous ABA as a germination inhibitor and dormancy can be restored by the application of ABA. Both natural (+)-ABA and its enantiomer (−)-ABA are equally effective in inhibiting germination when supplied to excised embryos of wheat (Walker-Simmons et al.[8], 1992). As shown in FIG. 12, (+)-8'-methylene ABA is at least 10 times more effective than natural ABA, with 1.0 μM (+)-8'-methylene ABA giving equivalent inhibition results to 10 μM (+)-ABA although we have not measured the metabolism of the analog in the embryos, the increased activity over ABA is likely due in part to greater persistence. These results support the conclusion that maintaining ABA levels in hydrated dormant grain embryos contributes to their growth arrest, and indicate that long-lasting ABA analogs, such as 8'-methylene ABA, will be useful tools to examine the role of ABA in both induction and maintenance of seed dormancy.

Figure 13:
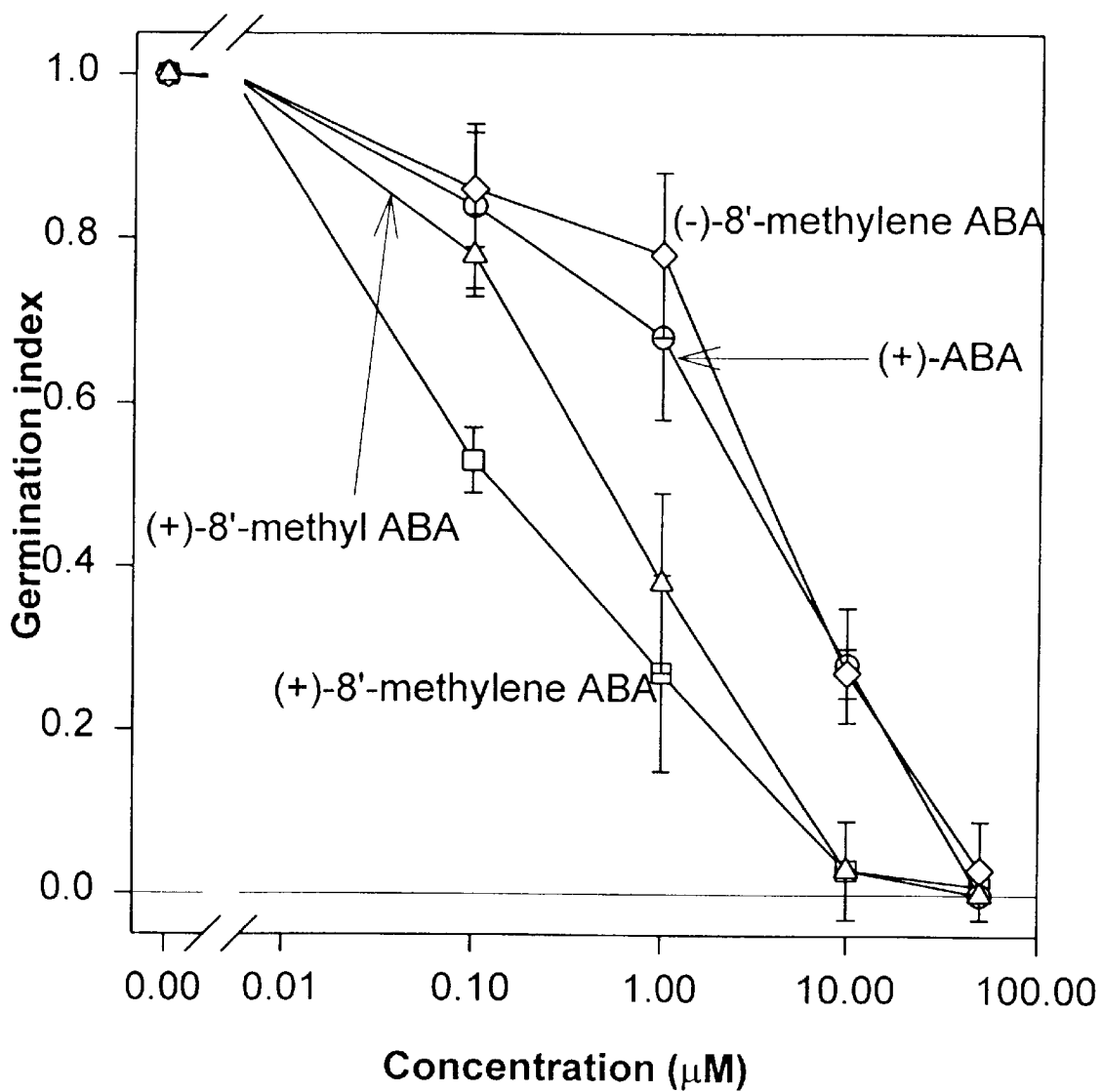
FIG. 13 is a graph which illustrates the biological activity of (+)-ABA, (+)-8'-methylene ABA, (−)-8'-methylene ABA, and (+)-8'-methyl ABA as germination inhibitors of excised wheat embryos.

Germination inhibitory activity was assessed for other 8'-ABA analogs including (−)-8'-methylene ABA (the mirror image, of (+)-8' methylene ABA), and (+)-8'-methyl ABA (FIG. 13). The (−)-8' methylene ABA is similar in potency to (+)-ABA. The (+)-8'- methyl ABA and (+)-8'-methylene ABA are both more active than (+)-ABA. The most potent compound over all concentrations and time points is (+)-8'-methylene ABA.

Cress Seed Germination

FIG. 5 shows the effect of two concentrations of (+)-[8']-methylene ABA and natural ABA on germination of cress seed. At 1 μM the 8'-Methylene analog is more potent than ABA, and at 5 M the seeds supplied with ABA begin to germinate, while analog-imbibed seed remain dormant. In summary, (+)-[8']-methylene ABA 4 is a more effective germination inhibitor in seeds of both a monocot and a dicot. It is anticipated that analog 4 will be more active than ABA in seed germination inhibition for species in which the hydroxylation of ABA to 8'-hydroxy ABA is the major pathway of degradation.

Biological Activity of 8'-Methylene ABA in Transpiration in Wheat Seedlings

ABA is a key signal molecule involved in regulating transpiration in plants. We had previously determined that esters were as active as acids in this assay (data not shown) so the effect of the methyl esters of natural ABA (+)-8'-methylene ABA and 8'-methyl ABA on transpiration in intact wheat seedlings was compared three hours after application. The most active analog is the 8'-methylene compound, which requires a concentration between 5–10 µM to reduce the transpiration rate of the wheat seedlings to 50% ($TR_{50}$), with the ABA ester causing 50% inhibition at concentrations between 25–50 M. The saturated 8'-side chain analog is relatively weak in this assay, with the 50% effective dose being 100 µM. This last result is very different from those reported by Nakano et al.[3], (1995) who showed that the saturated 8'-methyl analog is only slightly weaker than ABA in a stomatal opening assay. The difference in responses may be due to reduced uptake of the 8'-methyl ABA in the intact wheat seedling.

Biological Activity of 8'-methylene ABA in ABA-inducible Gene Expression

Figure 14:
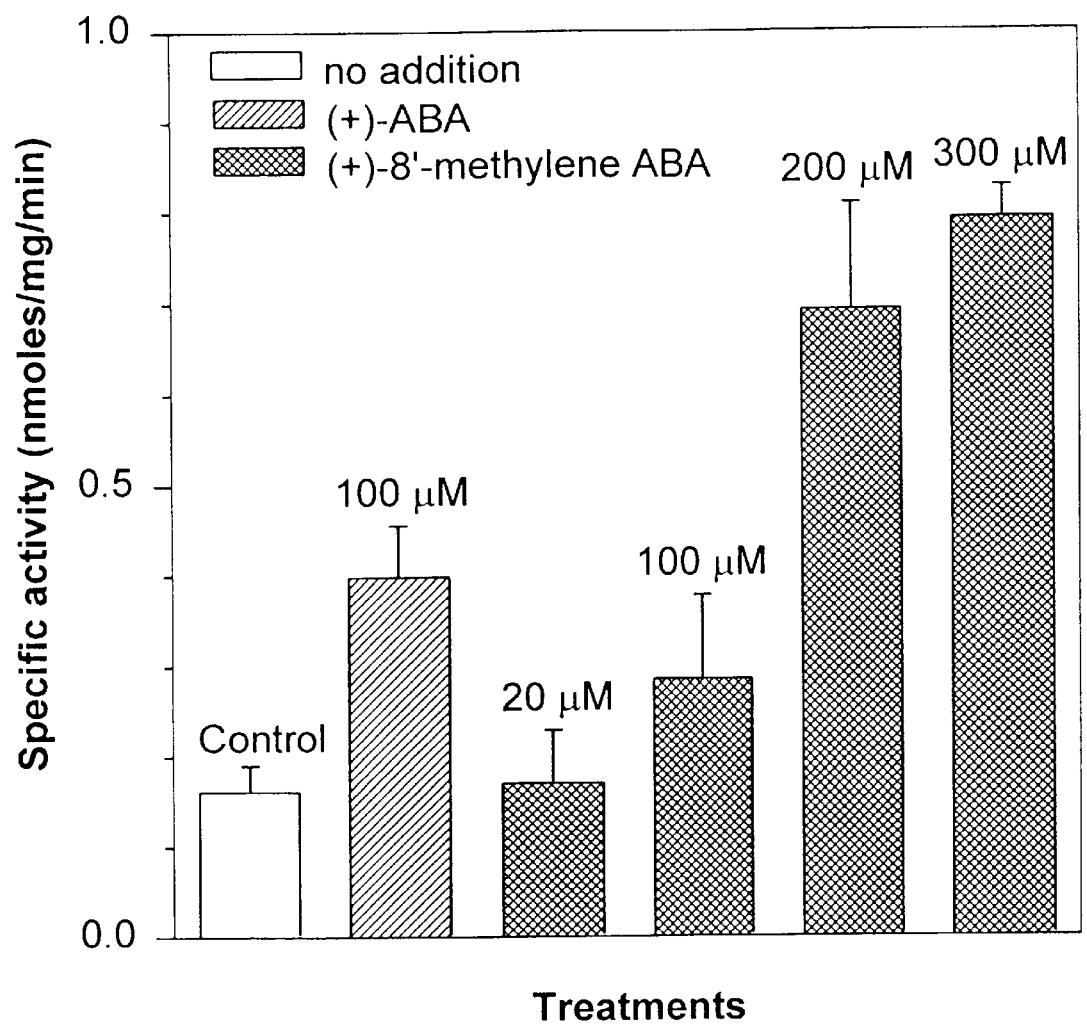
FIG. 14 is a graph which illustrates the effect of (+)-ABA and (+)-8'-methylene ABA on GUS specific activity in homogenates of cotyledons from homozygous tobacco seedlings containing the transgene Pcor6.6-GUS.
Figure 15:
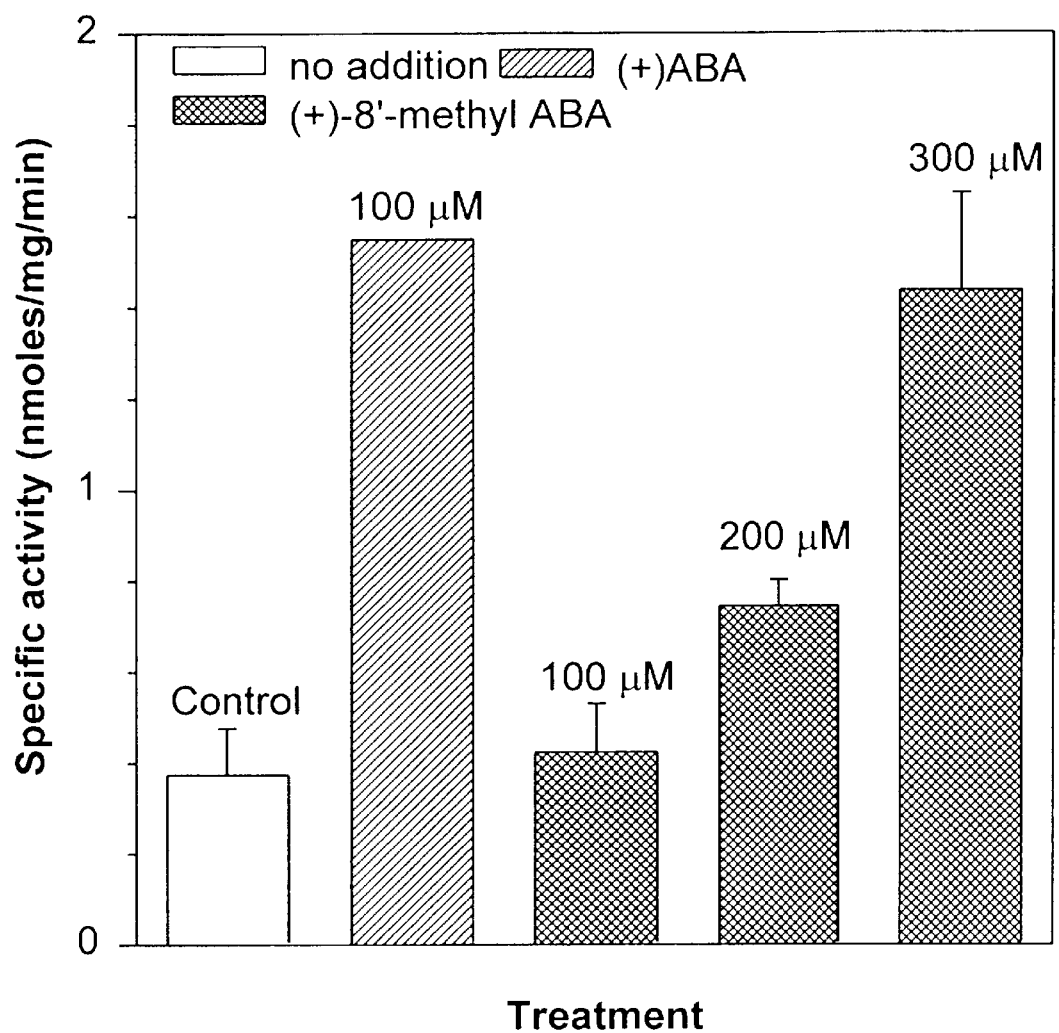
FIG. 15 is a graph which illustrates the effect of (+)-ABA and (+)-8'-methyl ABA on GUS specific activity in homogenates of cotyledons from homozygous tobacco seedlings containing the transgene Pcor6. 6-GUS.

FIGS. 14 and 15 show the induction of ABA-responsive gene expression in transgenic tobacco seedlings that were imbibed with (+)-ABA, (+)-8'-methylene ABA or (+)-8'-methyl ABA for 24 hours. The transgenic seedlings contained the ABA-responsive cor6.6 promoter from *Arabidopsis thaliana* (H. Wang et al., 1994) fused to the protein coding sequence of β-glucuronidase although at 100 µM, (+)-8'- methylene ABA was a slightly weaker inducer than ABA, the analog was highly effective in inducing ABA-responsive gene expression. 8'-Methyl ABA was about 3-fold weaker than ABA (FIG. 15).

In the following new compounds the 8'-carbon atom of ABA has been replaced either by an acetylene or by an acetylene bearing an additional methyl group. The general form of the compounds is shown below.

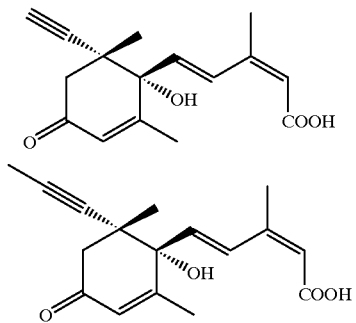

Figure 9:
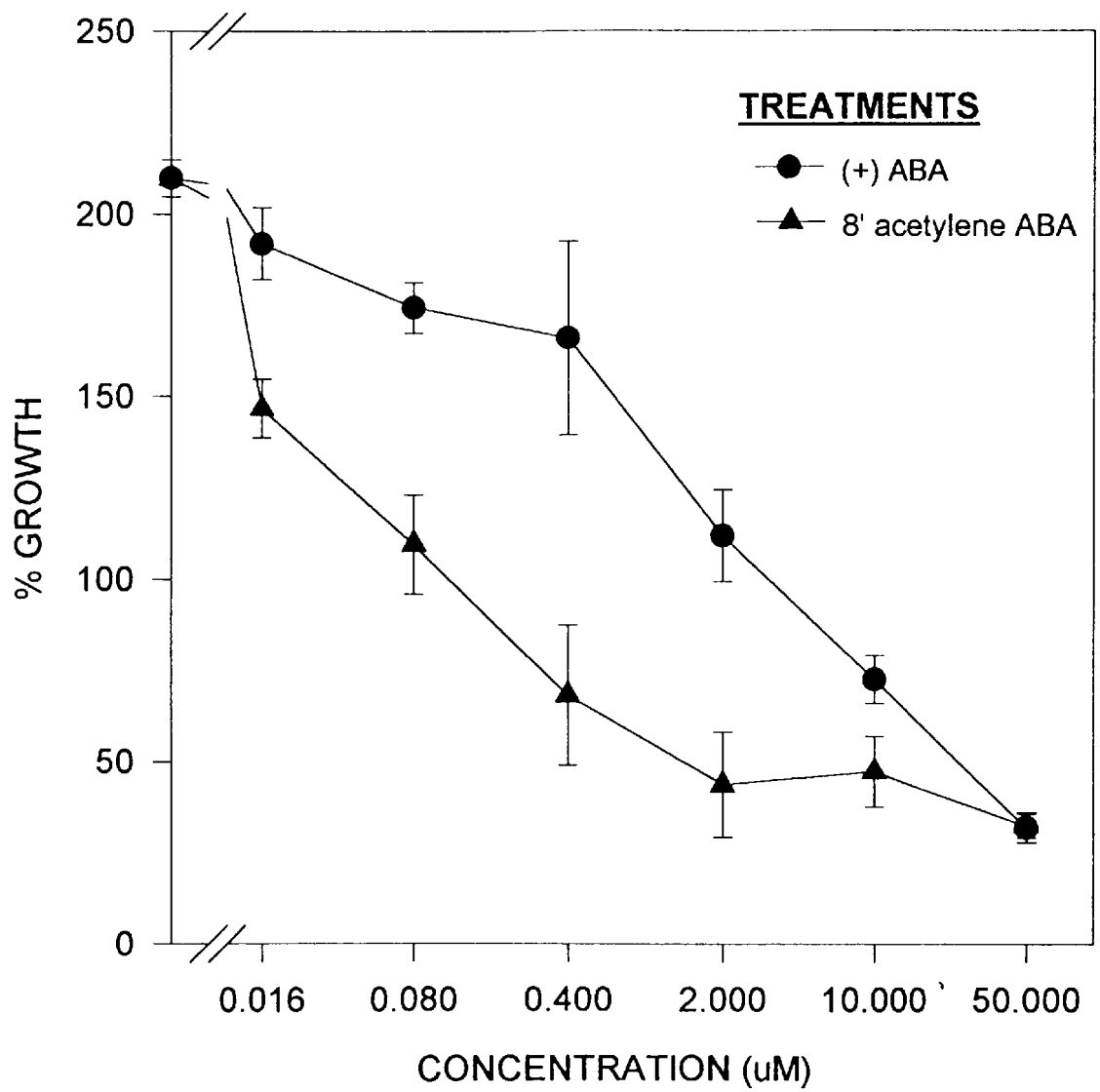
FIG. 9 is a graph which illustrates the corn growth inhibition of ABA and 8' acetylenic ABA.

The molecules are prepared from PBI252, as was the 8'-methylene ABA. The experimental procedures and spectral data of the new analogs are as follows. In the following experiment, the 8'-acetylene ABA was compared to ABA in growth inhibition of corn cells. As shown in FIG. 9, this new compound is more potent than ABA. Accordingly it will act as a hyper ABA.

8'-AcetyleneABA and 8'-MethylacetyleneABA

Methyl 8'-AcetyleneABA

To PBI 252 (500 mg) in dry THF (40 ml) at −78° C., was added ethynylmagnesium bromide (5 eq, 19.1 ml, 0.5M solution in THF). The solution was warmed to −20° C. and left for 16 hours. The reaction mixture was quenched with aqueous $NH_4Cl$ and extracted into ethyl acetate (3×30 ml). The combined organic extracts were washed with saturated NaCl solution, dried over $Na_2SO_4$, concentrated and purified by flash chromatography to give 360 mg of product. HREIMS: [M+] at m/z 289.1416 ($C_{17}H_{21}O_4$ requires 289.1440); IR $\nu_{max}$ cm$^{-1}$: 3286 (w, O—H), 1716.6, 1669.7 (C=O); $^1$H NMR: δ7.86 (d, 1H-4, J=16.1 Hz), 6.02 (t, 1H-3', J=1.1 Hz), 5.90 (d, 1H-4, J=16.1 Hz), 5.74 (s, 1H-2), 3.68 (s, $CO_2CH_3$), 2.64, (s, 1H-OH), 2.63 (dd, 1H-5', J=15.9, 0.9 Hz), 2.50 (d, 1H-5', J=16.8 Hz), 2.27 (s, 1H-HCC), 1.98 (d, 3H-6 or 3', J=1.1 Hz), 1.95 (d, 3H-6 or 3', J=1.4 Hz), 1.31 (s, 3H-9').

The ester could be separated into its two enantiomers using a Chiracel OD column (10% IPA in hexane 3 ml/min, injecting 20 mg per run). Peak with retention time of 25.5 min [α] $D^{20}$ =(+) 339.5 [0.43% in MeOH]. Peak with retention time of 36.3 min [α] $D^{20}$ =(−) 342.8 [0.35% in MeOH].

(+)-8'-AcetyleneABA

To a solution of the above (−)-ester (10 mg) in 1 ml of MeOH was added 2 ml of 2 M KOH. The mixture was stirred at room temperature for 4 h, at which time it was diluted with 5 ml $H_2O$ and washed with $CH_2Cl_2$ (3×20 ml). The organic layer was discarded and the aqueous layer acidified with 1M HCl and then extracted into $CH_2Cl_2$ (3×20 ml). The combined organic extracts were washed with saturated NaCl solution and dried over $Na_2SO_4$ to yield, after concentration, 7.9 mg (80% yield) of (+) -8' acetyleneABA. IR $\nu_{max}$ cm$^{-1}$: 3500–2500 (br, O—H), 1684 (C=O); $^1$H NMR: δ7.81 (d, 1H-4,J=16.2 Hz), 6.03 (s, 1H-3'), 5.95 (d, 1H4, J=16.1 Hz), 5.77 (s, 1H-2), 2.80, (br s, 1H-OH), 2.63 (d, 1H-5', J=17.0 Hz), 2.50 (d, 1H-5', J =16.9 Hz), 2.27 (s, 1H-HCC), 2.02 (d, 3H-6 or 3', J =0.7 Hz), 1.95 (d, 3H-6 or 3', J =1. Hz), 1.31 (s, 3H-9'). [α] $D^{25}$ =(+)-316.8 [0.51% in MeOH].

(−)-8' AcetyleneABA could be made in an analogous manner, and gave identical spectral data to the (+)-enantiomer, with the following change: [α] $D^{25}$ =(−)-296.9 [0.78% in MeOH].

Methyl 8'-MethylacetyleneABA

To PBI 252 (500 mg) in dry THF (40 ml) at −78° C., was added 1-propynylmagnesium bromide (5 eq, 19.1 ml, 0.5M solution in THF). The solution was warmed to −20° C. and left for 2 hours. The reaction mixture was quenched with aqueous $NH_4Cl$ and extracted into ethyl acetate (3×30 ml). The combined organic extracts were washed with saturated NaCl solution, dried over $Na_2SO_4$ and concentrated. The crude solid was recrystallized from ether, and the remaining mother liquor concentrated and purified by flash chromatography (25% ethyl acetate in hexane) to give 415 mg (72% yield) of product. HREIMS: [M+1]$^+$ at m/z 303.1609 ($C_{18}H_{23}O_4$ requires 303.1596); $^1$H NMR: δ7.81 (d, 1H-4, J=16.1 Hz), 5.98 (s, 1H-3'), 5.90(d, 1H-4, J =16.1 Hz), 5.72 (s, 1H-2), 3.66 (s, $CO_2CH_3$), 2.73, (s, 1H-OH), 2.55 (dd, 1H-5', J=16.6, 0.7 Hz ), 2.46 (d, 1H-5', J=16.7 Hz) , 1.97 (d, 3H-6 or 3', J=1.0 Hz), 1.92 (d, 3H-6 or 3', J=1.3 Hz), 1.75 (s, $3H-CH_3CC$), 1.24 (s, 3H-9').

The ester could be separated into its two enantiomers using a Chiracel OD column (20% IPA in hexane 3 ml/min). Peak with retention time of 12.7 min [α] $D^{25}$ =(+)350.8 [3.54% in $CHCl_3$]. Peak with retention time of 18.4 min [α] $D^{25}$ =(−)368.8 [3.35% in $CHCl_3$].

(+)-8'-MethylacetyleneABA

To a ice cold solution of the above (+)-ester (35 mg) in 7 ml of MeOH was added 7 ml of 2 M KOH. The mixture was stirred at room temperature for 4 h, at which time it was diluted with 5 ml $H_2O$ and washed with $CH_2Cl_2$ (3×20 ml). The organic layer was discarded and the aqueous layer acidified with 1M HCl and then extracted into $CH_2Cl_2$ (3×20 ml). The combined organic extracts were washed with saturated NaCl solution and dried over $Na_2SO_4$ to yield, after concentration, 30 mg of (+)-8'methylacetyleneABA. $^1$H NMR: 67 7.78 (d, 1H-4, J =16.2 Hz), 6.00 (s, 1H-3'), 5.95 (d, 1H-4, J=16.1 Hz), 5.74 (s, 1H-2), 2.80, (br s, 1H-OH), 2.56 (d, 1H-5', J=16.7 Hz), 2.46 (d, 1H-5', J=16.7 Hz), 2.01

(s, 3H-6 or 3'), 1.92 (d, 3H-6 or 3', J=0.9. Hz), 1.74 (s, 3H, CCCH$_3$), 1.24 (s, 3H-9'). $^{13}$C NMR: δ196.24, 170.62, 163.25, 151.21, 133.18, 130.17, 127.52, 118.36, 81.56, 80.59, 78.29, 47.99, 44.36, 23.53, 21.26, 19.25, 3.56. [α] D$^{25}$=(+)-364 [3.0% in MeOH].

(−)-8'-MethylacetyleneABA could be made in an analogous manner, and gave identical spectral data to the (+)-enantiomer, with the following change: [α] D$^{25}$ =(−)-383.8 [2.84% in MeOH].

Use of Methyl 8'-Methylene ABA

Canola Seed Emergence

Figure 16:
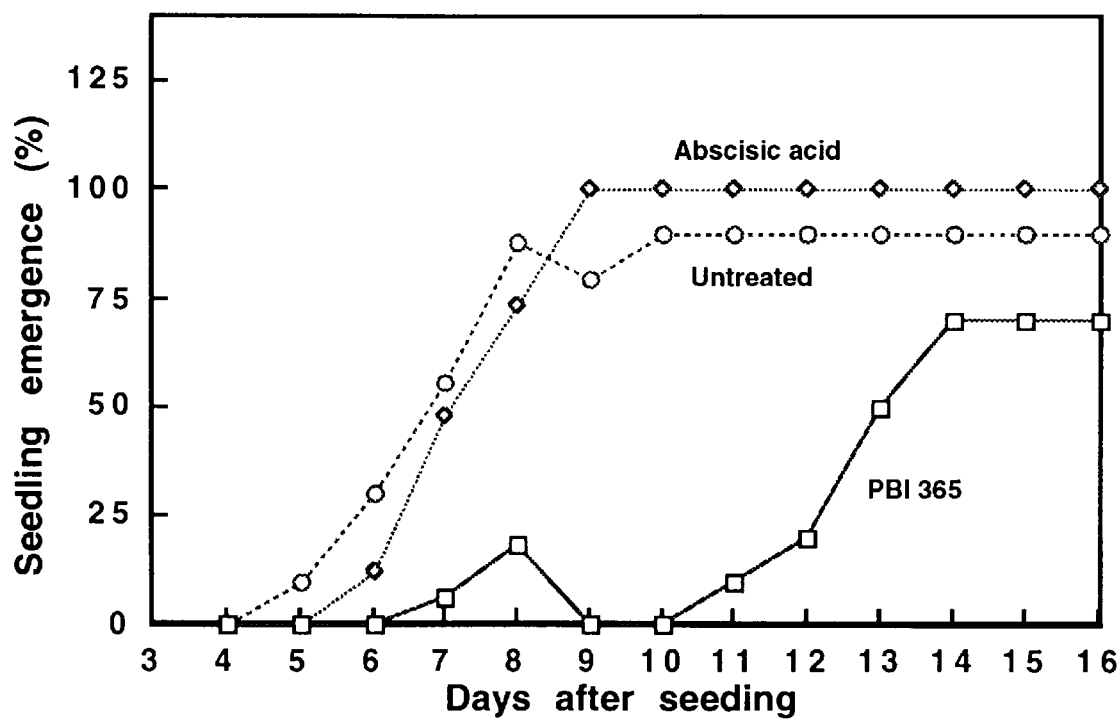
FIG. 16 is a graph which illustrates the effects of PBI-365 on Canola seed emergence.

Methyl 8'-methylene ABA (PBI-365) was applied to canola seed by evaporation of a 10$^3$M solution of the analog in MeOH under reduced pressure. The effects on germination control are shown in FIG. 16.

Methyl 8'-methylene ABA (PBI-365) for improving survival of transplanted spruce seedlings.

Figure 17:
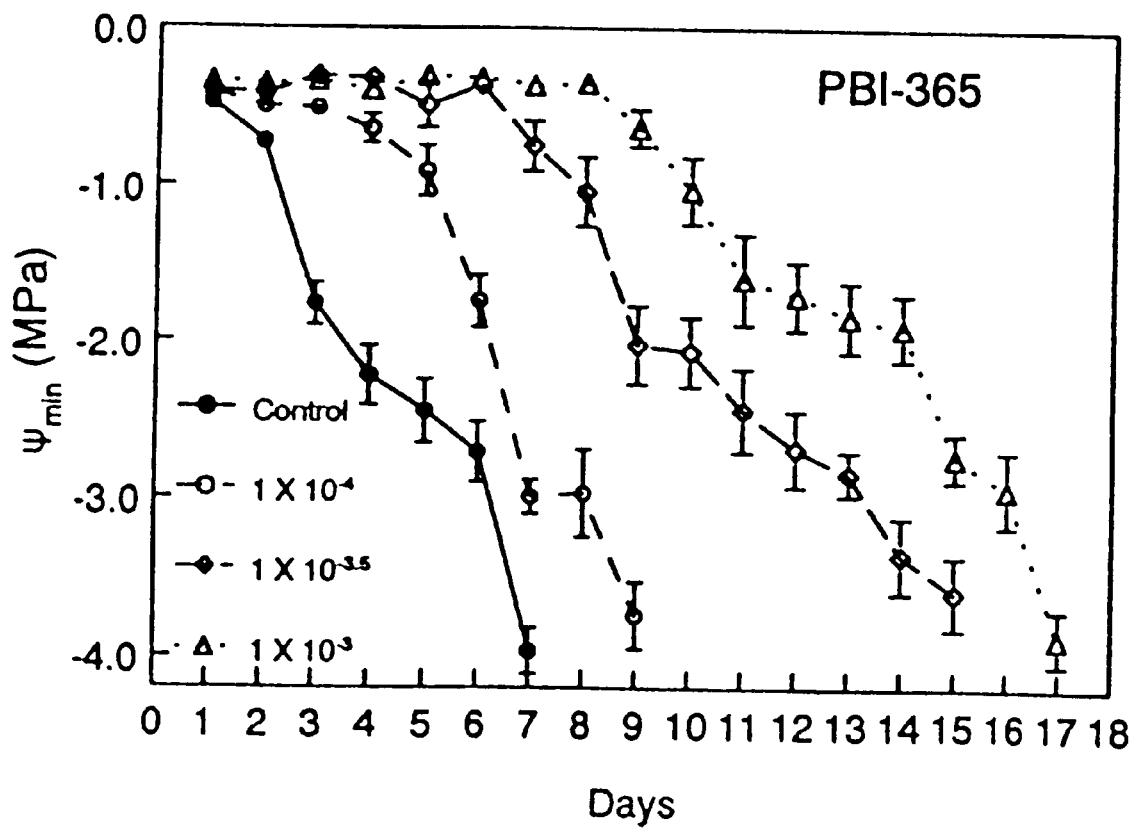
FIG. 17 is a graph which illustrates the survival of transplanted spruce seedlings to drought conditions, after treatment with methyl-8'-methylene ABA.

Interior spruce seedlings treated with ABA analog #365 had excellent drought avoidance capability under a range of drought conditions. This enhanced drought avoidance was due to a reduction in needle conductance and improved seedling water balance under drought conditions. The drought avoidance capability of this analog improved with higher treatment concentrations (FIG. 17).

Figure 18:
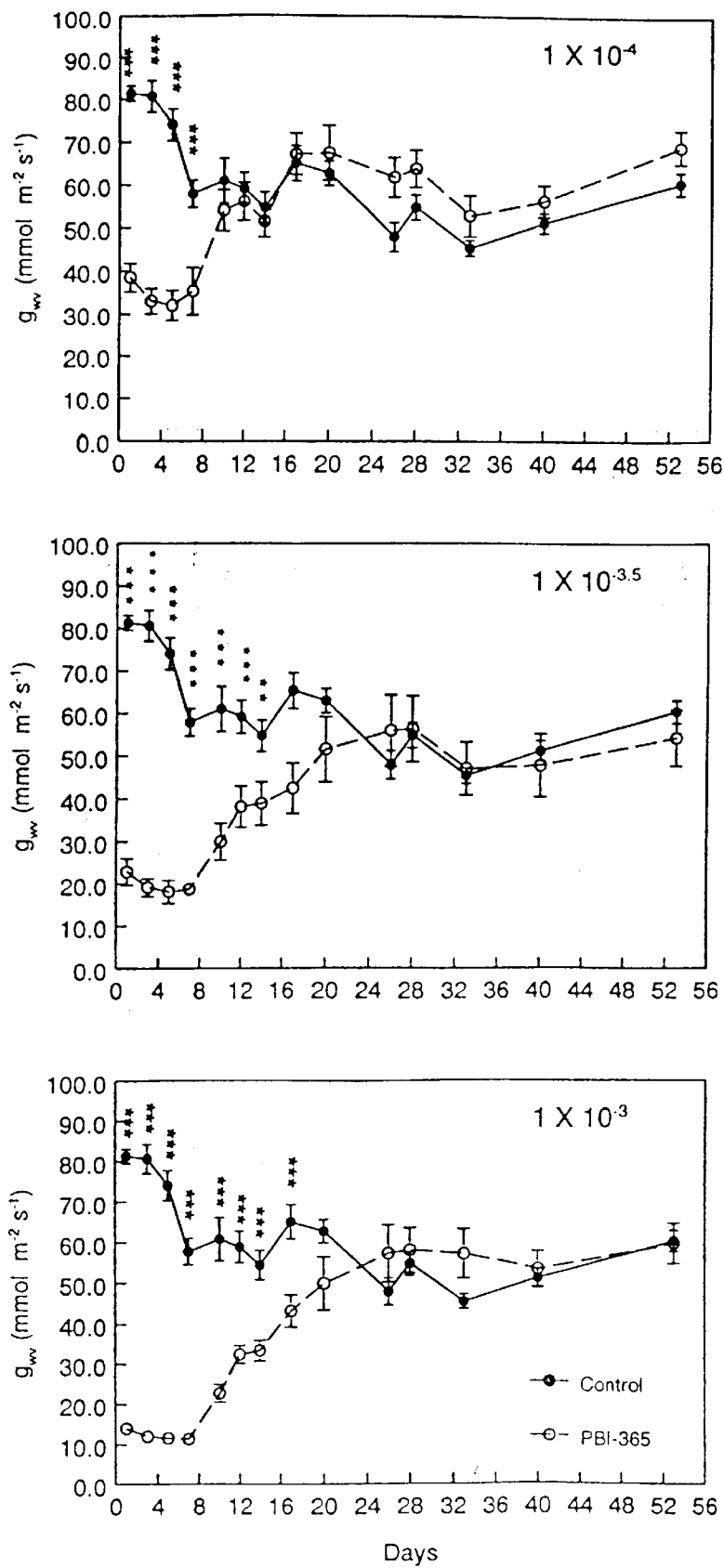
FIG. 18 to 21 are graphs which illustrate the effect of different concentrations of methyl-8'-methylene ABA on transplanted spruce seedlings.
Figure 19:
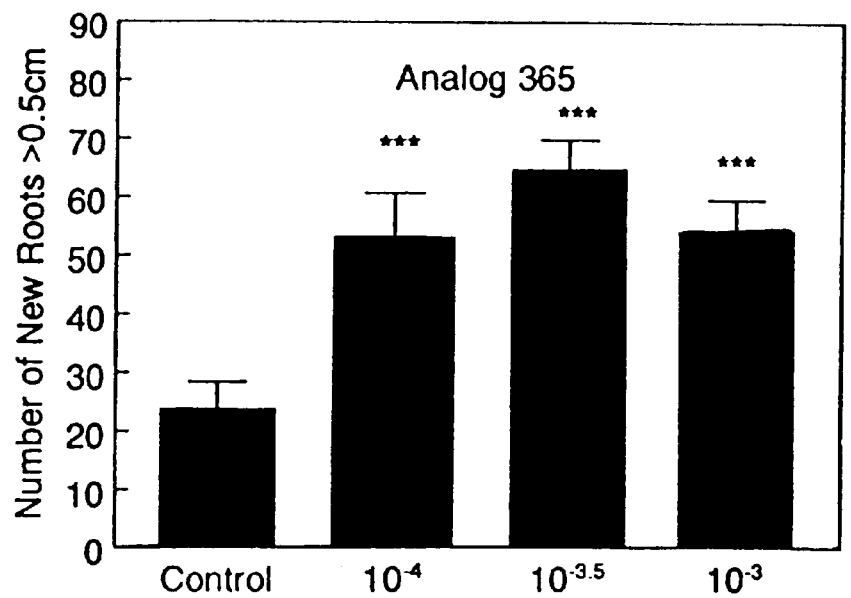
Figure 20:
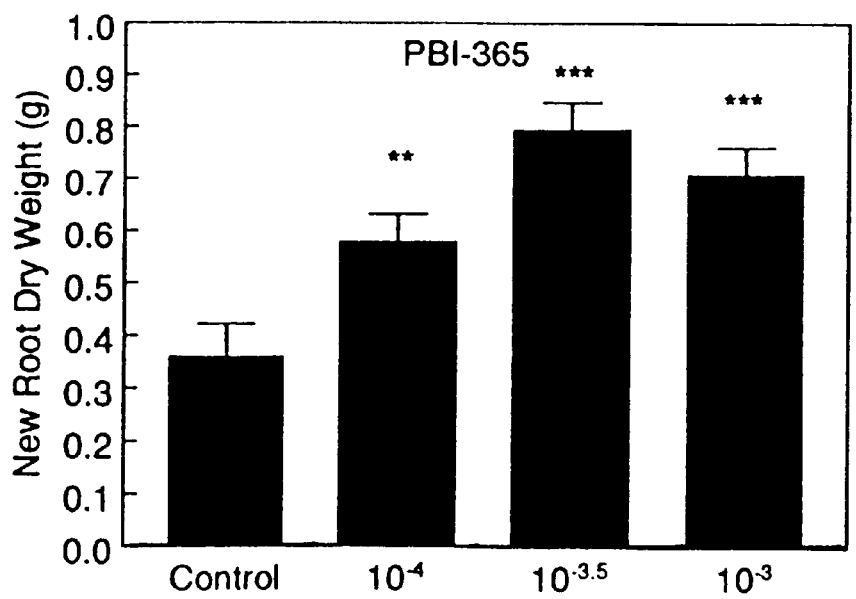
Figure 21:
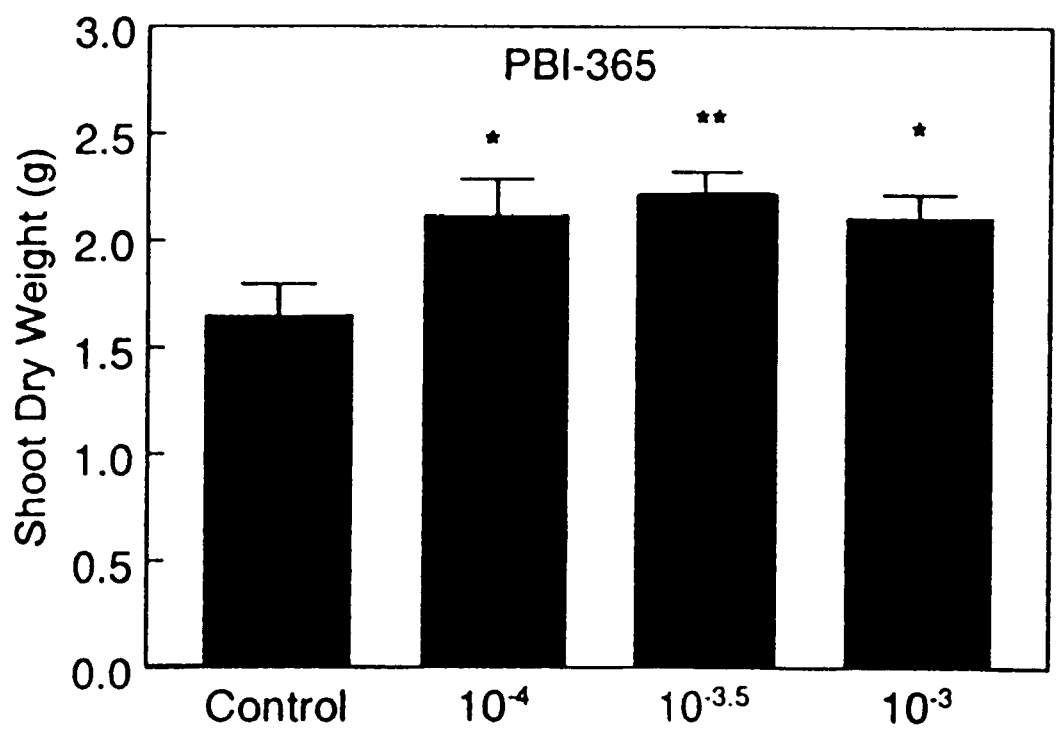

ABA analog #365 had no long term negative effects on growth of spring-and summer-plant interior spruce seedlings under optimum soil moisture conditions (FIG. 18). The ABA analog had no definitive effect on seedling growth under moderate and sever drought conditions, but a positive influence on growth when seedlings were exposed to near lethal drought conditions. The analog caused a one to three week reduction in the gas exchange capability of interior spruce seedlings under optimum conditions, with the longer periods of gas exchange reduction occurring at higher concentrations (FIGS. 19–21).

The ABA analog was applied as a spray-root drench that stimulated application through a nursery irrigation system. Seedlings with intact root-soil plugs were placed in a container, and ABA analog treatments were applied as a top drench. Treated seedlings were kept in the large container where the treatment flow-through was allowed to be re-absorbed into the plugs over a two day period. This ensured that all of the treatment was taken up by the root plugs and was available to seedlings. During testing, root-soil plugs were kept intact, enabling ABA analog treatments to be retained in close contact with the root system.

For this testing program, ABA analog #365 was applied at 10$^{-4}$, 10$^{3.5}$ and 10$^{-3}$M concentrations. Analogs were dissolved in an acetone solution (@ 1%) to prepare ABA analog treatments. In addition, there was a control treatment of acetone only @ 1%. The analog treatments were applied one time, two days before the start of experimental measurements. Each seedling received approximately 20 ml of either an analog or a control solution.

Gas exchange parameters (net photosynthesis (P$_n$), needle conductance (g$_{wv}$), water use efficiency-not reported) were determined on the seedlings treated with the ABA analog at each concentration (n=8). After application of ABA analogs, seedlings from each treatment (n=75) were potted in a peat-vermiculite growing media, and placed in a controlled environment growth room (air temperature at 24±3° C., 40±10% relative humidity, and an 20h photoperiod at 500 μmol m$^{-2}$s$^{-1}$). Gas exchange parameters were assessed 9 times across the first 20 days of the measurement period. Thereafter, gas exchange parameters were periodically assessed at 5 times from day 20 until the 52nd day of the measurement period.

Just after treatment application, seedlings (n=75) were put through a rapid eight to fifteen day drought. Seedlings were watered to saturation during ABA analog application. After 24 to 48 hours, when all of the ABA analog solution was absorbed by the seedling root plug, root systems were enclosed in a plastic bag and placed in a darkened chamber with the shoot systems exposed to the above described controlled environment conditions. Seedlings were allowed to dry out through shoot transpiration. Gas exchange parameters (P$_n$, and g$_{wv}$) of seedlings (n=8) from each treatment were measured during each daylight period. At each gas exchange measurement time, seedlings were measured with a pressure chamber to determine ψ, Changes in gas exchange parameters and seedling water balance were determined over time. Seedlings in all treatments were exposed to drought until the treatment population had a mean ψ$_{min}$ of <−4.0 Mpa or when P$_n$ was a negative value.

A study was conducted to determine how the ABA analog influenced seedling response to potentially lethal soil drought. It was hypothesized that ABA analogs limit water use and delay deleterious physiological conditions in seedlings under limited soil water availability. The ABA analog would allow seedlings to avoid a potentially lethal drought stress to survive and have normal morphological development.

Just after treatment application, seedlings (n=75) were put through a rapid drought. Over the drought, seedlings were measured with a pressure chamber to determine ψ. The drought ended for seedlings (n=25) in all treatments when the control treatment had a mean ψ$_{min}$ of <−4.0MPa for two days.

Literature Cited

1. Walker-Simmons M K, Rose P A, Shaw A C Abrams S R (1994) The 7'-methyl group of abscisic acid is critical for biological activity in wheat embryo germination. Plant Physiol 106: 1279–1284.
2. Todokori Y. Hirai N., Koshimuzu K. (1994) 8' and 9'-methoxyabscisic acids as antimetabolic analogs of abscisic acid. Biosci biotech Biochem 58: 707–715.
3. Nakano S, Todoroki Y, Hirai N, Ohigashi H. (1995) Synthesis and biological activity of 7'-, 8'-, and 9'-alkyl analogues of abscisic acid. Biosci Biotech Biochem 59: 1699–1706.
4. Todoroki Y. Hirai N, Koshimizu K (1995). 8', 8'-difluoro- and 8', 8', 8'- trifluoroabscisic acids as highly potent long lasting analogues of abscisic acid. Phytochem 38: 561–568.
5. Kim B T, Min Y K, Asami T, Park N K, Jeong I H, Cho K Y, Toshida S (1995) Synthesis and biological activities of new fluorinated abscisic acid. Bioorganic and Medicinal Chem Lett 5 275–278).
6. Balsevich J J, Cutler A J, Lamb N, Friesen L J, Kurz E U, Perras M, Abrams SR (1994) Response of cultured maize cells to (+)-abscisic acid, (−)-abscisic acid, and their metabolites. Plant Physiol 106: 135–142.
7. Rose P A, Lei B, Shaw A C, Barton, D L, Walker-Simmons M K, Abrams S R. (1996) Probing the role of the hydroxyl group of ABA: analogs with methyl ether at C-1'. Phytochem 41: 1251–1258.
8. Walker-Simmons M K, Anderburg R J, Rose P A, Abrams S R (1992) Optically pure abscisic acid analogs—tools for relating germination inhibition and gene expression in wheat embryos. Plant Physiol 99: 501–507.

We claim:
1. A compound of structural formula I

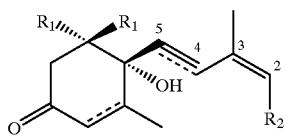

wherein one of $R_1$ is alkenyl, alkynyl, aryl or cycloalkenyl, and the other is methyl, and where the bond at the C4–C5 position is a double bond it is trans, and wherein the bond at C2–C3 is cis or trans, and $R_2$ is $CH_2OH$, CHO, COOH, or COO-alkyl, and wherein the cyclohexanone ring double bond may also be reduced.

2. A compound of structural formula Ia

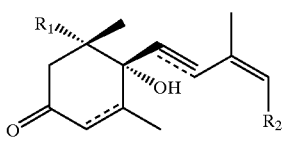

wherein, $R_1$ is alkenyl, alkynyl, aryl or cycloalkenyl and where the bond at the C4–C5 position is a double bond it is trans, and wherein the bond at C2–C3 is cis or trans, and $R_2$ is $CH_2OH$, CHO, COOH or COO-alkyl, and wherein the cyclohexanone ring double bond may also be reduced.

3. A compound according to claim 2, wherein structural formula Ia, $R_1$ is selected from the group consisting of $CH_2CH=CH_2$, $CH=CH_2$, CCH and $CH_2CCH$.

4. A compound of structural formula Ib

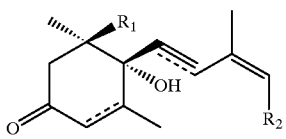

wherein, $R_1$ is alkenyl, alkynyl, aryl or cycloalkenyl, and where the bond at the C4–C5 position is a double bond it is trans, and wherein the bond at C2–C3 is cis or trans, and $R_2$ is $CH_2OH$, CHO, COOH, or COO-alkyl, and wherein the cyclohexanone ring double bond may also be reduced.

5. A compound according to claim 4, wherein structural formula Ib, $R_1$ is selected from the group consisting of $CH_2CH=CH_2$, $CH=CH_2$, $C\equiv CH$ and $CH_2CCH$.

6. The compound according to claim 2, of structural formula

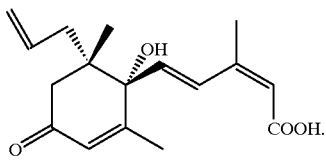

7. The compound according to claim 2, of structural formula

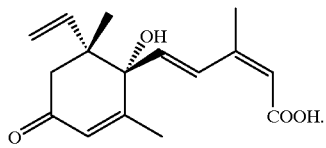

8. The compound according to claim 2, of structural formula

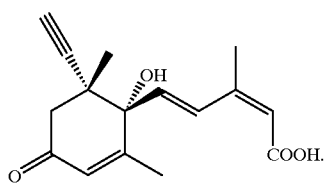

9. The compound according to claim 2 of structural formula

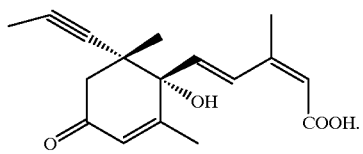

10. The compound according to claim 3, of structural formula

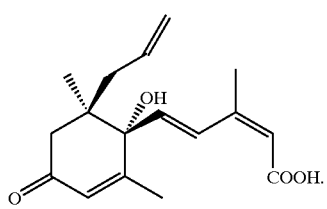

11. A method of making a compound of formula Ia,

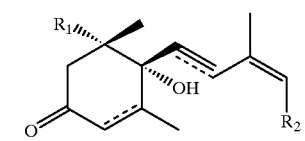

wherein, $R_1$ is alkenyl, alkynyl, aryl, cycloalkenyl, other further substituted carbon chain including deuterium containing residues, and carbon containing substituents with heteroatoms and halogens; and when the bond at C4–C5 positions is a double bond it is trans and wherein the double bond at C2–C3 is cis or trans, and $R_2$ is $CH_2OH$, CHO, COOH, COO-alkyl, or derivatives thereof, and wherein the cyclohexanone ring double bond may also be reduced, comprising
  (a) reacting 2,6-dimethylcylohexa-2,5-dien-1,4-dione or a derivative thereof, with the dianion of 3-methylpent-2-en-4-yn-1-ol or a hydroxyl protected derivative thereof, in the presence of a Grignard reagent of formula $R_1MgX$ wherein X is Cl, Br or I, to effect conjugate addition of the unsaturated group, and where required (b) reduction of the C4-C5 triple bond to the trans double bond, and oxidation of the C1 hydroxyl to form functional derivatives thereof, and (c) when non-chiral starting material is employed, separating the (+) and (−) isomers by HPLC, and (d) further modification of the 8'-position by selective ozonolysis, and subsequent Wittig-type reactions onto the formed alehyde of 8'-methylene ABA.

12. A method of making a compound of formula Ib,

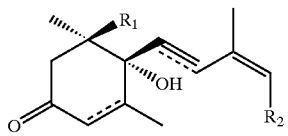

Ib wherein, $R_1$ is alkenyl, alkynyl, aryl, cycloalkenyl, other further substituted carbon chain including deuterium containing residues, and carbon containing substituents with heteroatoms and halogens; and when the bond at C4–C5 positions is a double bond it is trans and wherein the double bond at C2–C3 is cis or trans, and $R_2$ is $CH_2OH$, CHO, COOH, COO-alkyl, or derivatives thereof, and wherein the cyclohexanone ring double bond may also be reduced, comprising reacting (a) 2,6-dimethyl-4,4-ethylenedioxycyclohex-2-enone with $R_1$-I, (b) reacting the product so formed with the dianion of 3-methyl-pent-2-en-4-yn-1-ol, and where required (c) reduction of the C4–C5 triple bond to a double bond, and oxidation of the C1 alcohol to form functional derivatives thereof, and (d) separating the 8'-and 9'-$R_1$ esters by HPLC.

13. A method according to claim 11 or 12, wherein step (a) the dione is used as starting material.

14. A method according to claim 11 or 12, wherein step (a) the C4-ketal of the dione is used as starting material.

15. A method according to claim 11, wherein step (a) a catalyst is included.

16. A method according to claim 15, wherein the catalyst is copper iodide.

17. A method according to any one of claims 11, 12, 15 or 16, wherein $R_1$ is selected from the group consisting of $CH_2CH=CH_2$, $CH=CH_2$, $C\equiv CH$, and $CH_2CCH$.

18. A method of affecting physiological processes in plants, known to be affected by natural ABA, comprising applying to the plant an effective amount of a compound as defined in any one of claims 1 to 10.

19. A method for the control of plant seed germination, comprising applying to the plant an effective amount of a compound as defined in any one of claims 1 to 10.

20. A method of enhancing antitranspirant activity in plants, comprising applying to the plant an effective amount of a compound as defined in any one of claims 1 to 10.

21. A method of enhancing ABA-inducible gene expression in plants, comprising applying to the plant an effective amount of a compound as defined in any one of claims 1 to 10.

22. A method of reducing transplantation shock in plant seedlings, comprising applying to the plant an effective amount of compounds as defined in any one of claims 1 to 10.

23. The method according to claim 22, wherein the plant is a spruce seedling, and the compound is applied as a root spray in a concentration of $10^{-3}$ to $10^{-4}$ M in an organic solvent.

* * * * *